(12) United States Patent
Farrell et al.

(10) Patent No.: US 9,011,114 B2
(45) Date of Patent: Apr. 21, 2015

(54) MEDICAL FLUID DELIVERY SETS AND RELATED SYSTEMS AND METHODS

(75) Inventors: Sean Farrell, Fresno, CA (US); Joseph Michael Fallon, Dixon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 333 days.

(21) Appl. No.: 13/412,182

(22) Filed: Mar. 5, 2012

(65) Prior Publication Data

US 2012/0230844 A1    Sep. 13, 2012

Related U.S. Application Data

(60) Provisional application No. 61/450,887, filed on Mar. 9, 2011.

(51) Int. Cl.
*F04B 9/02* (2006.01)
*A61M 1/28* (2006.01)

(52) U.S. Cl.
CPC .. *F04B 9/02* (2013.01); *A61M 1/28* (2013.01); *A61M 2205/12* (2013.01)

(58) Field of Classification Search
CPC ................ A61M 2205/125; A61M 2205/126; A61M 2205/127; A61M 1/28; A61M 2205/12; F04B 9/02; F04B 43/12
USPC ........ 604/28, 29, 151, 131; 417/412, 415, 45, 417/477.2; 433/89
See application file for complete search history.

(56) References Cited

U.S. PATENT DOCUMENTS

| | | |
|---|---|---|
| 329,773 A | 11/1885 | Perry |
| 2,383,193 A | 8/1945 | Herbert |
| 2,529,028 A | 11/1950 | Landon |
| 2,658,526 A | 11/1953 | Porter |
| 2,711,134 A | 6/1955 | Hughes |
| 2,755,745 A | 7/1956 | Lewis |
| 2,871,795 A | 2/1959 | Smith |
| 2,886,281 A | 5/1959 | Canalizo |
| 3,083,943 A | 4/1963 | Stewart, Jr. et al. |

(Continued)

FOREIGN PATENT DOCUMENTS

| | | |
|---|---|---|
| CA | 2101232 A | 1/1983 |
| DE | 2628238 | 1/1978 |

(Continued)

OTHER PUBLICATIONS

Gambro®, "DEHP-free cartridge blood sets," © Nov. 2004, Gambro, Inc., Lakewood, CO, 4 pp.

(Continued)

*Primary Examiner* — Devon Kramer
*Assistant Examiner* — Jon Hoffmann
(74) *Attorney, Agent, or Firm* — Fish & Richardson P.C.

(57) ABSTRACT

This disclosure relates to medical fluid delivery sets and related systems and methods. In some aspects of the invention, a medical fluid cassette includes a plunger slidably disposed within a recess of a base of the cassette such that a substantially liquid-tight seal is maintained between the plunger and the base as the plunger slides axially within the recess. The plunger and the base cooperate to at least partially define a fluid pump chamber. When the plunger is displaced in a first direction, fluid is forced out of the fluid pump chamber, and when the plunger is displaced in a second direction, fluid is drawn into the fluid pump chamber.

27 Claims, 18 Drawing Sheets

(56) References Cited

U.S. PATENT DOCUMENTS

| | | | |
|---|---|---|---|
| 3,323,786 | A | 6/1967 | Boschi |
| 3,556,465 | A | 1/1971 | Little |
| 3,689,025 | A | 9/1972 | Kiser et al. |
| 3,741,687 | A | 6/1973 | Nystroem |
| 3,927,955 | A | 12/1975 | Spinosa et al. |
| 3,966,358 | A | 6/1976 | Heimes et al. |
| 3,985,135 | A | 10/1976 | Carpenter et al. |
| 4,026,669 | A | 5/1977 | Leonard et al. |
| 4,047,844 | A | 9/1977 | Robinson |
| 4,091,812 | A | 5/1978 | Helixon et al. |
| 4,121,584 | A | 10/1978 | Turner et al. |
| 4,152,098 | A | 5/1979 | Moody et al. |
| 4,158,530 | A | 6/1979 | Bernstein |
| 4,178,940 | A | 12/1979 | Au |
| 4,273,121 | A | 6/1981 | Jassawalla |
| 4,303,376 | A | 12/1981 | Siekmann |
| 4,304,260 | A | 12/1981 | Turner et al. |
| 4,322,201 | A | 3/1982 | Archibald |
| 4,333,452 | A | 6/1982 | Au |
| 4,370,983 | A | 2/1983 | Lichtenstein |
| 4,382,753 | A | 5/1983 | Archibald |
| 4,410,322 | A | 10/1983 | Archibald |
| 4,412,553 | A | 11/1983 | Kopp et al. |
| 4,436,620 | A | 3/1984 | Bellotti et al. |
| 4,453,932 | A | 6/1984 | Pastrone |
| 4,479,760 | A | 10/1984 | Bilstad et al. |
| 4,479,761 | A | 10/1984 | Bilstad et al. |
| 4,479,762 | A | 10/1984 | Bilstad et al. |
| 4,490,621 | A | 12/1984 | Watabe et al. |
| 4,536,201 | A | 8/1985 | Brorsson et al. |
| 4,558,715 | A | 12/1985 | Walton et al. |
| 4,569,378 | A | 2/1986 | Bergandy |
| 4,583,920 | A | 4/1986 | Lindner |
| 4,597,412 | A | 7/1986 | Stark |
| 4,623,328 | A | 11/1986 | Hartranft |
| 4,628,499 | A | 12/1986 | Hammett |
| 4,639,245 | A | 1/1987 | Pastrone et al. |
| 4,643,713 | A | 2/1987 | Viitala |
| 4,657,490 | A | 4/1987 | Abbott |
| 4,662,598 | A | 5/1987 | Weingarten |
| 4,662,906 | A | 5/1987 | Matkovich et al. |
| 4,676,467 | A | 6/1987 | Palsulich |
| 4,690,621 | A | 9/1987 | Swain |
| 4,703,913 | A | 11/1987 | Hunkapiller |
| 4,705,259 | A | 11/1987 | Dolhen et al. |
| 4,710,166 | A | 12/1987 | Thompson et al. |
| 4,735,558 | A | 4/1988 | Kienholz et al. |
| 4,778,451 | A | 10/1988 | Kamen |
| 4,808,161 | A | 2/1989 | Kamen |
| 4,826,482 | A | 5/1989 | Kamen |
| 4,840,542 | A | 6/1989 | Abbott |
| 4,842,584 | A | 6/1989 | Pastrone |
| 4,846,636 | A | 7/1989 | Danby et al. |
| 4,850,980 | A * | 7/1989 | Lentz et al. .................. 604/248 |
| 4,858,883 | A | 8/1989 | Webster |
| 4,902,282 | A | 2/1990 | Bellotti et al. |
| 4,906,260 | A | 3/1990 | Emheiser et al. |
| 4,927,411 | A | 5/1990 | Pastrone et al. |
| 4,950,134 | A | 8/1990 | Bailey et al. |
| 4,974,754 | A | 12/1990 | Wirz |
| 4,976,162 | A | 12/1990 | Kamen |
| 4,995,864 | A | 2/1991 | Bartholomew et al. |
| 4,997,464 | A | 3/1991 | Kopf |
| 5,002,471 | A | 3/1991 | Perlov |
| 5,006,050 | A | 4/1991 | Cooke et al. |
| 5,036,886 | A | 8/1991 | Olsen et al. |
| 5,061,236 | A | 10/1991 | Sutherland et al. |
| 5,088,515 | A | 2/1992 | Kamen |
| 5,098,262 | A | 3/1992 | Wecker et al. |
| 5,100,380 | A | 3/1992 | Epstein |
| 5,100,699 | A | 3/1992 | Roeser |
| 5,116,021 | A | 5/1992 | Faust et al. |
| 5,116,316 | A | 5/1992 | Sertic et al. |
| 5,146,713 | A | 9/1992 | Grafius |
| 5,151,019 | A | 9/1992 | Danby et al. |
| 5,167,837 | A | 12/1992 | Snodgrass et al. |
| 5,171,029 | A | 12/1992 | Maxwell et al. |
| 5,178,182 | A | 1/1993 | Kamen |
| 5,193,990 | A | 3/1993 | Kamen et al. |
| 5,211,201 | A | 5/1993 | Kamen et al. |
| 5,241,985 | A | 9/1993 | Faust et al. |
| 5,247,434 | A | 9/1993 | Peterson et al. |
| 5,249,932 | A | 10/1993 | Van Bork |
| 5,252,044 | A | 10/1993 | Raines et al. |
| 5,259,352 | A | 11/1993 | Gerhardy et al. |
| 5,267,956 | A | 12/1993 | Beuchat |
| 5,279,556 | A | 1/1994 | Goi et al. |
| 5,302,093 | A | 4/1994 | Owens et al. |
| 5,324,422 | A | 6/1994 | Colleran et al. |
| 5,330,425 | A | 7/1994 | Utterberg |
| 5,342,182 | A | 8/1994 | Montoya et al. |
| 5,344,292 | A | 9/1994 | Rabenau et al. |
| 5,350,357 | A | 9/1994 | Kamen et al. |
| D351,470 | S | 10/1994 | Scherer et al. |
| 5,353,837 | A | 10/1994 | Faust |
| 5,378,126 | A | 1/1995 | Abrahamson et al. |
| 5,395,351 | A | 3/1995 | Munsch |
| 5,413,626 | A | 5/1995 | Bartsch |
| 5,415,528 | A | 5/1995 | Ogden et al. |
| 5,421,208 | A | 6/1995 | Packard et al. |
| 5,421,823 | A | 6/1995 | Kamen et al. |
| 5,427,509 | A | 6/1995 | Chapman et al. |
| 5,431,626 | A | 7/1995 | Bryant et al. |
| 5,431,627 | A | 7/1995 | Pastrone et al. |
| 5,431,634 | A | 7/1995 | Brown |
| 5,438,510 | A | 8/1995 | Bryant et al. |
| 5,441,636 | A | 8/1995 | Chevallet et al. |
| 5,445,506 | A | 8/1995 | Afflerbaugh et al. |
| 5,447,286 | A | 9/1995 | Kamen et al. |
| 5,462,416 | A | 10/1995 | Dennehey et al. |
| 5,462,417 | A | 10/1995 | Chapman |
| 5,474,683 | A | 12/1995 | Bryant et al. |
| 5,478,211 | A | 12/1995 | Dominiak et al. |
| 5,480,294 | A | 1/1996 | Di Perna et al. |
| 5,482,438 | A | 1/1996 | Anderson et al. |
| 5,482,440 | A | 1/1996 | Dennehey et al. |
| 5,482,446 | A | 1/1996 | Williamson et al. |
| 5,484,239 | A | 1/1996 | Chapman et al. |
| 5,486,286 | A | 1/1996 | Peterson et al. |
| 5,514,069 | A | 5/1996 | Brown et al. |
| 5,538,405 | A | 7/1996 | Patno et al. |
| 5,540,568 | A | 7/1996 | Rosen et al. |
| 5,547,453 | A | 8/1996 | Di Perna |
| 5,551,850 | A | 9/1996 | Williamson et al. |
| 5,551,941 | A | 9/1996 | Howell |
| 5,551,942 | A | 9/1996 | Brown et al. |
| 5,554,013 | A | 9/1996 | Owens et al. |
| 5,570,716 | A | 11/1996 | Kamen et al. |
| 5,573,385 | A | 11/1996 | Chevallier |
| 5,578,070 | A | 11/1996 | Utterberg |
| 5,588,816 | A * | 12/1996 | Abbott et al. .................. 417/479 |
| 5,593,290 | A | 1/1997 | Greisch et al. |
| 5,609,572 | A | 3/1997 | Lang |
| 5,614,677 | A | 3/1997 | Wamsiedler et al. |
| 5,628,908 | A | 5/1997 | Kamen et al. |
| 5,630,710 | A | 5/1997 | Tune et al. |
| 5,634,896 | A | 6/1997 | Bryant et al. |
| 5,640,995 | A | 6/1997 | Packard et al. |
| 5,641,405 | A | 6/1997 | Keshaviah et al. |
| 5,641,892 | A | 6/1997 | Larkins et al. |
| 5,643,205 | A | 7/1997 | Utterberg |
| 5,645,531 | A | 7/1997 | Thompson et al. |
| 5,658,133 | A | 8/1997 | Anderson et al. |
| 5,669,764 | A | 9/1997 | Behringer et al. |
| 5,690,602 | A | 11/1997 | Brown et al. |
| D390,654 | S | 2/1998 | Alsberg et al. |
| 5,713,865 | A | 2/1998 | Manning et al. |
| 5,713,888 | A | 2/1998 | Neuenfeldt et al. |
| 5,718,567 | A | 2/1998 | Rapp et al. |
| 5,741,125 | A | 4/1998 | Neftel et al. |
| 5,746,708 | A | 5/1998 | Giesler et al. |
| 5,755,683 | A | 5/1998 | Houle et al. |
| 5,764,034 | A | 6/1998 | Bowman et al. |
| 5,769,387 | A | 6/1998 | Perez |

(56) References Cited

U.S. PATENT DOCUMENTS

| | | |
|---|---|---|
| 5,771,914 A | 6/1998 | Ling et al. |
| 5,772,635 A | 6/1998 | Dastur et al. |
| 5,772,637 A | 6/1998 | Heinzmann et al. |
| 5,775,371 A | 7/1998 | Pan et al. |
| 5,782,575 A | 7/1998 | Vincent et al. |
| 5,782,805 A | 7/1998 | Meinzer et al. |
| 5,799,207 A | 8/1998 | Wang et al. |
| 5,816,779 A | 10/1998 | Lawless et al. |
| 5,840,151 A | 11/1998 | Munsch |
| 5,842,841 A | 12/1998 | Danby et al. |
| 5,843,035 A | 12/1998 | Bowman et al. |
| 5,868,696 A | 2/1999 | Giesler et al. |
| 5,873,853 A | 2/1999 | Keilman et al. |
| 5,902,096 A | 5/1999 | Behringer et al. |
| 5,906,598 A | 5/1999 | Giesler et al. |
| 5,921,951 A | 7/1999 | Morris |
| 5,925,011 A | 7/1999 | Faict et al. |
| 5,934,885 A | 8/1999 | Farrell et al. |
| 5,935,099 A | 8/1999 | Peterson et al. |
| 5,938,634 A | 8/1999 | Packard |
| 5,984,897 A | 11/1999 | Petersen et al. |
| 5,989,423 A | 11/1999 | Kamen |
| 5,993,174 A | 11/1999 | Konishi |
| 5,996,634 A | 12/1999 | Dennehey et al. |
| 6,013,057 A | 1/2000 | Danby et al. |
| 6,036,668 A | 3/2000 | Mathis |
| 6,036,680 A | 3/2000 | Horne et al. |
| 6,041,801 A | 3/2000 | Gray et al. |
| 6,053,191 A | 4/2000 | Hussey |
| 6,065,389 A | 5/2000 | Riedlinger |
| 6,065,941 A | 5/2000 | Gray et al. |
| 6,068,612 A | 5/2000 | Bowman et al. |
| 6,074,359 A | 6/2000 | Keshaviah et al. |
| 6,079,959 A | 6/2000 | Kingsford et al. |
| 6,099,492 A | 8/2000 | Le Boeuf |
| 6,106,246 A | 8/2000 | Steck et al. |
| 6,110,410 A | 8/2000 | Owens et al. |
| 6,118,207 A | 9/2000 | Ormerod et al. |
| 6,129,517 A | 10/2000 | Danby et al. |
| 6,132,187 A | 10/2000 | Ericson |
| 6,136,565 A | 10/2000 | Best et al. |
| 6,152,705 A | 11/2000 | Kennedy et al. |
| 6,154,605 A | 11/2000 | Aonuma |
| 6,164,621 A | 12/2000 | Bouchard et al. |
| 6,165,154 A | 12/2000 | Gray et al. |
| 6,168,394 B1 | 1/2001 | Forman et al. |
| 6,178,996 B1 | 1/2001 | Suzuki |
| 6,179,801 B1 | 1/2001 | Holmes et al. |
| 6,184,356 B1 | 2/2001 | Anderson et al. |
| 6,189,857 B1 | 2/2001 | Zeger et al. |
| 6,196,987 B1 | 3/2001 | Holmes et al. |
| 6,200,287 B1 | 3/2001 | Keller et al. |
| 6,206,644 B1 | 3/2001 | Pereira et al. |
| 6,208,107 B1 | 3/2001 | Maske et al. |
| 6,210,361 B1 | 4/2001 | Kamen et al. |
| 6,220,295 B1 | 4/2001 | Bouchard et al. |
| 6,223,130 B1 | 4/2001 | Gray et al. |
| 6,227,807 B1 | 5/2001 | Chase |
| 6,227,824 B1 | 5/2001 | Stehr |
| 6,228,047 B1 | 5/2001 | Dadson |
| 6,229,753 B1 | 5/2001 | Kono et al. |
| 6,231,537 B1 | 5/2001 | Holmes et al. |
| 6,234,989 B1 | 5/2001 | Brierton et al. |
| 6,250,502 B1 | 6/2001 | Cote et al. |
| 6,261,065 B1 | 7/2001 | Nayak et al. |
| 6,267,242 B1 | 7/2001 | Nagata et al. |
| 6,270,673 B1 | 8/2001 | Belt et al. |
| 6,280,406 B1 | 8/2001 | Dolecek et al. |
| 6,281,145 B1 | 8/2001 | Deguchi et al. |
| 6,284,142 B1 | 9/2001 | Muller |
| 6,285,155 B1 | 9/2001 | Maske et al. |
| 6,286,566 B1 | 9/2001 | Cline et al. |
| 6,294,094 B1 | 9/2001 | Muller et al. |
| 6,296,450 B1 | 10/2001 | Westberg et al. |
| 6,297,322 B1 | 10/2001 | Ding et al. |
| 6,315,707 B1 | 11/2001 | Smith et al. |
| 6,315,754 B1 * | 11/2001 | Daoud et al. ............... 604/23 |
| 6,316,864 B1 | 11/2001 | Ormerod |
| 6,322,488 B1 | 11/2001 | Westberg et al. |
| 6,325,775 B1 | 12/2001 | Thom et al. |
| 6,337,049 B1 | 1/2002 | Tamari |
| RE37,553 E | 2/2002 | Ciavarini et al. |
| 6,343,614 B1 | 2/2002 | Gray et al. |
| 6,348,156 B1 | 2/2002 | Vishnoi et al. |
| 6,361,518 B1 | 3/2002 | Brierton et al. |
| 6,364,857 B1 | 4/2002 | Gray et al. |
| 6,367,669 B1 | 4/2002 | Au et al. |
| 6,382,923 B1 | 5/2002 | Gray |
| 6,383,158 B1 | 5/2002 | Utterberg |
| 6,402,486 B1 | 6/2002 | Steck et al. |
| 6,406,276 B1 | 6/2002 | Normand et al. |
| 6,409,696 B1 | 6/2002 | Toavs et al. |
| 6,416,293 B1 | 7/2002 | Bouchard et al. |
| 6,419,822 B2 | 7/2002 | Muller et al. |
| 6,455,676 B1 | 9/2002 | Weickert et al. |
| 6,471,855 B1 | 10/2002 | Odak et al. |
| 6,481,980 B1 | 11/2002 | Vandlik et al. |
| 6,484,383 B1 | 11/2002 | Herklotz |
| 6,489,896 B1 | 12/2002 | Platt et al. |
| 6,491,656 B1 | 12/2002 | Morris |
| 6,494,694 B2 | 12/2002 | Lawless et al. |
| 6,497,674 B1 | 12/2002 | Steele et al. |
| 6,497,676 B1 | 12/2002 | Childers et al. |
| 6,503,062 B1 | 1/2003 | Gray et al. |
| 6,514,225 B1 | 2/2003 | Utterberg et al. |
| 6,519,569 B1 | 2/2003 | White et al. |
| 6,520,747 B2 | 2/2003 | Gray et al. |
| 6,524,231 B1 | 2/2003 | Westberg et al. |
| 6,529,573 B2 | 3/2003 | Olsher et al. |
| 6,537,445 B2 | 3/2003 | Muller |
| 6,542,761 B1 | 4/2003 | Jahn et al. |
| 6,558,343 B1 | 5/2003 | Neftel |
| 6,572,604 B1 | 6/2003 | Platt et al. |
| 6,579,253 B1 | 6/2003 | Burbank et al. |
| 6,592,542 B2 | 7/2003 | Childers et al. |
| 6,595,948 B2 | 7/2003 | Suzuki et al. |
| 6,603,229 B1 | 8/2003 | Toye, IV |
| 6,604,908 B1 | 8/2003 | Bryant et al. |
| 6,645,166 B2 | 11/2003 | Scheunert et al. |
| 6,645,177 B1 * | 11/2003 | Shearn ............... 604/155 |
| 6,648,861 B2 | 11/2003 | Platt et al. |
| 6,663,359 B2 | 12/2003 | Gray |
| 6,670,323 B1 | 12/2003 | Looker et al. |
| 6,672,841 B1 | 1/2004 | Herklotz et al. |
| 6,695,593 B1 | 2/2004 | Steck et al. |
| 6,695,803 B1 | 2/2004 | Robinson et al. |
| 6,709,417 B1 | 3/2004 | Houle et al. |
| 6,716,004 B2 | 4/2004 | Vandlik et al. |
| 6,723,062 B1 | 4/2004 | Westberg et al. |
| 6,725,726 B1 | 4/2004 | Adolfs et al. |
| 6,726,656 B2 | 4/2004 | Kamen et al. |
| 6,730,055 B2 | 5/2004 | Bainbridge et al. |
| 6,743,201 B1 | 6/2004 | Doenig et al. |
| 6,746,514 B2 | 6/2004 | Bedingfield et al. |
| 6,749,403 B2 | 6/2004 | Bryant et al. |
| 6,752,172 B2 | 6/2004 | Lauer |
| 6,752,599 B2 | 6/2004 | Park |
| 6,755,801 B2 | 6/2004 | Utterberg et al. |
| 6,758,975 B2 | 7/2004 | Peabody et al. |
| 6,759,007 B1 | 7/2004 | Westberg et al. |
| 6,759,014 B2 | 7/2004 | Dales et al. |
| 6,764,460 B2 | 7/2004 | Dolecek et al. |
| 6,764,761 B2 | 7/2004 | Eu et al. |
| 6,768,425 B2 | 7/2004 | Flaherty et al. |
| 6,774,517 B2 | 8/2004 | Kowalski et al. |
| 6,790,014 B2 | 9/2004 | Bowen |
| 6,790,195 B2 | 9/2004 | Steele et al. |
| 6,790,198 B1 | 9/2004 | White et al. |
| 6,800,054 B2 | 10/2004 | Westberg et al. |
| 6,808,369 B2 | 10/2004 | Gray et al. |
| 6,814,547 B2 | 11/2004 | Childers et al. |
| 6,821,432 B2 | 11/2004 | Metzner |
| 6,828,125 B1 | 12/2004 | Hoffman et al. |
| 6,846,161 B2 | 1/2005 | Kline et al. |

(56) References Cited

U.S. PATENT DOCUMENTS

| | | |
|---|---|---|
| 6,852,090 B2 | 2/2005 | Burbank et al. |
| 6,869,538 B2 | 3/2005 | Yu et al. |
| 6,905,479 B1 | 6/2005 | Bouchard et al. |
| 6,929,751 B2 | 8/2005 | Bowman, Jr. et al. |
| 6,939,111 B2 | 9/2005 | Huitt et al. |
| 6,949,079 B1 | 9/2005 | Westberg et al. |
| 6,953,323 B2 | 10/2005 | Childers et al. |
| 6,957,952 B1 | 10/2005 | Steck et al. |
| 6,984,218 B2 | 1/2006 | Nayak et al. |
| 7,021,148 B2 | 4/2006 | Kuhn et al. |
| 7,029,245 B2 | 4/2006 | Maianti et al. |
| 7,033,539 B2 | 4/2006 | Krensky et al. |
| 7,041,076 B1 | 5/2006 | Westberg et al. |
| 7,044,432 B2 | 5/2006 | Beden et al. |
| 7,049,406 B2 | 5/2006 | Weickert et al. |
| 7,083,719 B2 | 8/2006 | Bowman, Jr. et al. |
| 7,087,036 B2 | 8/2006 | Busby et al. |
| 7,107,837 B2 | 9/2006 | Lauman et al. |
| 7,115,107 B2 | 10/2006 | Delnevo et al. |
| 7,115,228 B2 | 10/2006 | Lundtveit et al. |
| 7,147,613 B2 | 12/2006 | Burbank et al. |
| 7,153,286 B2 | 12/2006 | Busby et al. |
| 7,160,087 B2 | 1/2007 | Fathallah et al. |
| 7,166,231 B2 | 1/2007 | Westberg et al. |
| 7,175,606 B2 | 2/2007 | Bowman et al. |
| 7,195,607 B2 | 3/2007 | Westberg et al. |
| 7,211,560 B2 | 5/2007 | Looker et al. |
| 7,232,435 B2 | 6/2007 | Hildebrand et al. |
| 7,236,936 B2 | 6/2007 | White et al. |
| 7,238,164 B2 | 7/2007 | Childers et al. |
| 7,255,680 B1 | 8/2007 | Gharib |
| 7,258,534 B2 | 8/2007 | Fathallah et al. |
| 7,261,559 B2 * | 8/2007 | Smith et al. ............... 433/90 |
| 7,267,661 B2 | 9/2007 | Susi |
| 7,273,465 B2 | 9/2007 | Ash |
| 7,306,578 B2 | 12/2007 | Gray et al. |
| 7,331,935 B2 | 2/2008 | Barere |
| 7,338,469 B2 | 3/2008 | Barker et al. |
| 7,338,472 B2 | 3/2008 | Shearn |
| 7,345,025 B2 | 3/2008 | Symonds et al. |
| 7,347,836 B2 | 3/2008 | Peterson et al. |
| 7,390,311 B2 | 6/2008 | Hildebrand et al. |
| 7,398,183 B2 | 7/2008 | Holland et al. |
| 7,399,637 B2 | 7/2008 | Wright et al. |
| 7,404,809 B2 | 7/2008 | Susi |
| 7,410,475 B2 | 8/2008 | Krensky et al. |
| 7,422,905 B2 | 9/2008 | Clague et al. |
| 7,454,314 B2 | 11/2008 | Holland et al. |
| 7,461,968 B2 | 12/2008 | Demers et al. |
| 7,490,021 B2 | 2/2009 | Holland et al. |
| 7,500,962 B2 | 3/2009 | Childers et al. |
| 7,517,387 B2 | 4/2009 | Chevallet et al. |
| 7,553,295 B2 | 6/2009 | Susi |
| 7,556,616 B2 | 7/2009 | Fathallah et al. |
| 7,575,564 B2 | 8/2009 | Childers |
| 7,618,948 B2 | 11/2009 | Kaemmerer |
| 7,645,258 B2 | 1/2010 | White et al. |
| 7,648,627 B2 | 1/2010 | Beden et al. |
| 7,654,976 B2 | 2/2010 | Peterson et al. |
| 7,662,286 B2 | 2/2010 | Childers et al. |
| 7,699,966 B2 | 4/2010 | Qin et al. |
| 7,717,682 B2 | 5/2010 | Orr |
| 7,789,849 B2 | 9/2010 | Busby et al. |
| 7,815,595 B2 | 10/2010 | Busby et al. |
| 8,038,640 B2 | 10/2011 | Orr |
| 8,197,231 B2 | 6/2012 | Orr |
| 8,197,439 B2 | 6/2012 | Wang et al. |
| 8,206,338 B2 | 6/2012 | Childers et al. |
| 8,292,594 B2 | 10/2012 | Tracey et al. |
| 8,366,921 B2 | 2/2013 | Beden et al. |
| 8,409,441 B2 | 4/2013 | Wilt |
| 8,562,834 B2 | 10/2013 | Kamen et al. |
| 8,721,879 B2 | 5/2014 | van der Merwe et al. |
| 2001/0034502 A1 | 10/2001 | Moberg |
| 2001/0037763 A1 | 11/2001 | Deguchi et al. |
| 2002/0045851 A1 | 4/2002 | Suzuki et al. |
| 2002/0062109 A1 | 5/2002 | Lauer |
| 2002/0072718 A1 | 6/2002 | Brugger et al. |
| 2002/0107474 A1 | 8/2002 | Noack |
| 2002/0141529 A1 | 10/2002 | Olsher et al. |
| 2002/0147423 A1 | 10/2002 | Burbank et al. |
| 2003/0018395 A1 | 1/2003 | Crnkovich et al. |
| 2003/0028144 A1 | 2/2003 | Duchon et al. |
| 2003/0029451 A1 | 2/2003 | Blair et al. |
| 2003/0042181 A1 | 3/2003 | Metzner |
| 2003/0100882 A1 | 5/2003 | Beden et al. |
| 2003/0136189 A1 | 7/2003 | Lauman et al. |
| 2003/0194332 A1 | 10/2003 | Jahn et al. |
| 2003/0200812 A1 | 10/2003 | Kuhn et al. |
| 2003/0204162 A1 | 10/2003 | Childers et al. |
| 2003/0217957 A1 | 11/2003 | Bowman et al. |
| 2003/0217961 A1 | 11/2003 | Hopping |
| 2003/0217975 A1 | 11/2003 | Yu et al. |
| 2003/0218623 A1 | 11/2003 | Krensky et al. |
| 2003/0220599 A1 | 11/2003 | Lundtveit et al. |
| 2003/0220605 A1 | 11/2003 | Bowman et al. |
| 2003/0220607 A1 | 11/2003 | Busby et al. |
| 2003/0220608 A1 | 11/2003 | Huitt et al. |
| 2003/0220609 A1 | 11/2003 | Childers et al. |
| 2003/0220627 A1 | 11/2003 | Distler et al. |
| 2004/0001766 A1 | 1/2004 | Maianti et al. |
| 2004/0010223 A1 | 1/2004 | Busby et al. |
| 2004/0019313 A1 | 1/2004 | Childers et al. |
| 2004/0019320 A1 | 1/2004 | Childers et al. |
| 2004/0031756 A1 | 2/2004 | Suzuki et al. |
| 2004/0064080 A1 | 4/2004 | Cruz et al. |
| 2004/0067161 A1 | 4/2004 | Axelsson |
| 2004/0082903 A1 | 4/2004 | Micheli |
| 2004/0084647 A1 | 5/2004 | Beden et al. |
| 2004/0109769 A1 | 6/2004 | Jahn et al. |
| 2004/0115068 A1 | 6/2004 | Hansen et al. |
| 2004/0135078 A1 | 7/2004 | Mandro et al. |
| 2004/0136843 A1 | 7/2004 | Jahn et al. |
| 2004/0156745 A1 | 8/2004 | Vandlik et al. |
| 2004/0195190 A1 | 10/2004 | Min et al. |
| 2004/0238416 A1 | 12/2004 | Burbank et al. |
| 2005/0054968 A1 | 3/2005 | Giannella |
| 2005/0230292 A1 | 10/2005 | Beden et al. |
| 2006/0002823 A1 | 1/2006 | Feldstein |
| 2006/0079766 A1 * | 4/2006 | Neer et al. ............... 600/432 |
| 2006/0079826 A1 | 4/2006 | Beden et al. |
| 2006/0195064 A1 | 8/2006 | Plahey et al. |
| 2007/0112297 A1 * | 5/2007 | Plahey et al. ............... 604/28 |
| 2007/0149913 A1 | 6/2007 | Busby et al. |
| 2007/0193940 A1 | 8/2007 | Duchamp et al. |
| 2007/0213651 A1 | 9/2007 | Busby et al. |
| 2007/0213653 A1 | 9/2007 | Childers et al. |
| 2007/0269340 A1 | 11/2007 | Dannenmaier et al. |
| 2008/0033346 A1 | 2/2008 | Childers et al. |
| 2008/0077068 A1 | 3/2008 | Orr |
| 2008/0125693 A1 * | 5/2008 | Gavin et al. ............... 604/29 |
| 2008/0208103 A1 | 8/2008 | Demers et al. |
| 2008/0216898 A1 | 9/2008 | Grant et al. |
| 2008/0253912 A1 | 10/2008 | Demers et al. |
| 2009/0004033 A1 | 1/2009 | Demers et al. |
| 2009/0099498 A1 | 4/2009 | Demers et al. |
| 2009/0137940 A1 | 5/2009 | Orr |
| 2009/0169402 A1 | 7/2009 | Stenberg |
| 2009/0212248 A1 | 8/2009 | Kozak |
| 2010/0211044 A1 | 8/2010 | Dacquay et al. |
| 2010/0241062 A1 | 9/2010 | Morris et al. |
| 2010/0286614 A1 | 11/2010 | Ring |
| 2011/0015610 A1 | 1/2011 | Plahey et al. |
| 2011/0092895 A1 | 4/2011 | Yardimci et al. |
| 2011/0125085 A1 | 5/2011 | McGill et al. |
| 2011/0137237 A1 | 6/2011 | Prisco et al. |
| 2011/0293450 A1 | 12/2011 | Grimes et al. |
| 2012/0065581 A1 | 3/2012 | Childers et al. |
| 2012/0123322 A1 | 5/2012 | Scarpaci et al. |
| 2012/0209169 A1 | 8/2012 | Morris et al. |
| 2012/0224984 A1 | 9/2012 | Orr |
| 2012/0232469 A1 | 9/2012 | Medina |
| 2012/0271226 A1 | 10/2012 | Farrell et al. |
| 2012/0308412 A1 | 12/2012 | Rochat |

(56) References Cited

U.S. PATENT DOCUMENTS

| | | |
|---|---|---|
| 2013/0118961 A1 | 5/2013 | Beden et al. |
| 2013/0118970 A1 | 5/2013 | Beden et al. |
| 2013/0184638 A1 | 7/2013 | Scarpaci et al. |
| 2013/0330208 A1 | 12/2013 | Ly et al. |
| 2013/0331774 A1 | 12/2013 | Farrell et al. |

FOREIGN PATENT DOCUMENTS

| | | |
|---|---|---|
| DE | 2827648 | 1/1979 |
| DE | 4006785 | 9/1990 |
| DE | 4336336 | 5/1994 |
| DE | 19837667 | 3/2000 |
| DE | 19919572 A1 | 11/2000 |
| DE | 10042324 | 2/2002 |
| DE | 10046651 | 4/2002 |
| DE | 19919572 C2 | 4/2002 |
| DE | 10053441 | 5/2002 |
| DE | 69618766 | 8/2002 |
| DE | 10143137 | 4/2003 |
| DE | 10157924 | 6/2003 |
| DE | 102007059239 | 6/2009 |
| EP | 0257279 | 3/1988 |
| EP | 0314379 | 8/1991 |
| EP | 0410125 B1 | 8/1993 |
| EP | 0728509 | 8/1996 |
| EP | 0848193 | 6/1998 |
| EP | 0856321 | 8/1998 |
| EP | 0947814 | 10/1999 |
| EP | 0956876 | 11/1999 |
| EP | 1529545 | 5/2005 |
| GB | 1483702 | 8/1977 |
| GB | 2101232 | 1/1983 |
| GB | 2331796 | 6/1999 |
| JP | 0396850 A | 4/1991 |
| JP | 04191755 | 7/1992 |
| JP | 06154314 | 6/1994 |
| JP | 06002650 | 11/1994 |
| JP | 08028722 | 2/1996 |
| JP | 11347115 | 12/1999 |
| JP | 2000070358 | 3/2000 |
| JP | 2000346214 | 12/2000 |
| WO | 8402473 | 7/1984 |
| WO | 8601115 | 2/1986 |
| WO | WO 9415660 A1 * | 7/1994 |
| WO | 9420155 | 9/1994 |
| WO | 9625064 | 8/1996 |
| WO | 9716214 | 5/1997 |
| WO | 9737703 | 10/1997 |
| WO | 9822165 | 5/1998 |
| WO | WO9822167 A1 | 5/1998 |
| WO | 0023140 | 4/2000 |
| WO | 0033898 | 6/2000 |
| WO | 0117605 | 3/2001 |
| WO | 0225146 | 3/2002 |
| WO | 0225225 | 3/2002 |
| WO | WO2007006030 A3 | 6/2007 |
| WO | 2009071069 | 6/2009 |
| WO | WO2011045167 A1 | 4/2011 |

OTHER PUBLICATIONS

Gambro®, Prisma® HF 1000, "For Increased Filtration Capacity", © Aug. 2001, Gambro Renal Products, Inc., Lakewood, CO, 2 pp.

Gambro®, "Prisma® M60 and M100 Pre-Pump Infusion Sets—Introducing: The unique solution that enables Physicians to choose a predilution method that meets the needs of their patients", © 2004, Gambro Inc., Lakewood, CO, 4 pp.

Glenn Avolio, "Principles of Rotary Optical Encoders," Sensors Journal of Machine Perception, vol. 10, No. 4, pp. 10-18, 1993.

Manns, Markus et al., "The acu-men: A new device for continuous renal replacement therapy in acute renal failure," Kidney International, vol. 54, pp. 268-274, 1998.

Liberty Cycler Operator's Manual, 2003-2004.

Newton IQ Cycler Operator Manual, Part No. 470203 Rev. F, 2000-2006.

Operator's Instructions, Fresenius 90/2 Peritoneal Therapy Cycler, Part No. 470016, Rev. B, 1991.

Operator's Manual, Serena, Program Version 3.xx—English, 2002.

Sleep Safe Operating Instructions, Software Version 0.9, Part No. 677 801 1; Aug. 2000.

Sleep Safe Technical Manual, Part No. 677 807 1; Aug. 2000.

Bolegoh, Gordon, "Pumps: Reference Guide", p. 24, 3rd edition, 2001.

Ronco et al., "Evolution of Machines for Automated Peritoneal Dialysis", in Automated Peritoneal Dialysis, Contributions to Nephrology, vol. 129, pp. 142-161, 1999.

Sleep Safe Operating Instructions, Software Version 0.5, Apr. 1999.

Sleep Safe Operating Instructions, Software Version 1.0, Oct. 2000.

Sleep Safe Technical Manual, Dec. 2001.

Sleep Safe Operating Instructions, Jan. 2002.

Sleep Safe Communicating Therapy, Mar. 1998.

Sleep Safe Kommunizierte Therapie, May 1998.

Innovative Technologies in Peritoneal Dialysis, Sleep Safe Concept, Oct. 13, 1999 (4 attachments).

TL™ Pump Brochure, TL Systems Corporation.

* cited by examiner

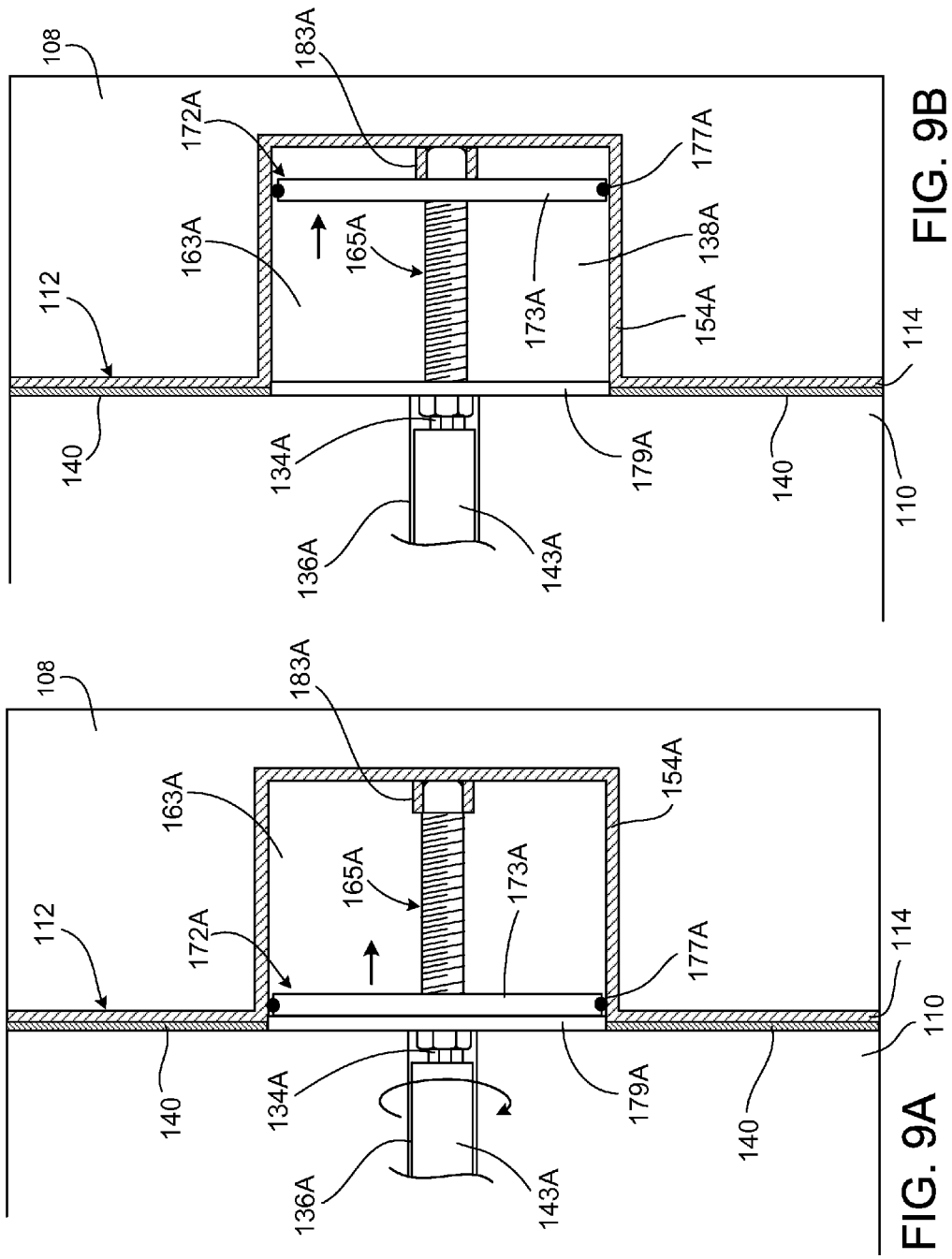

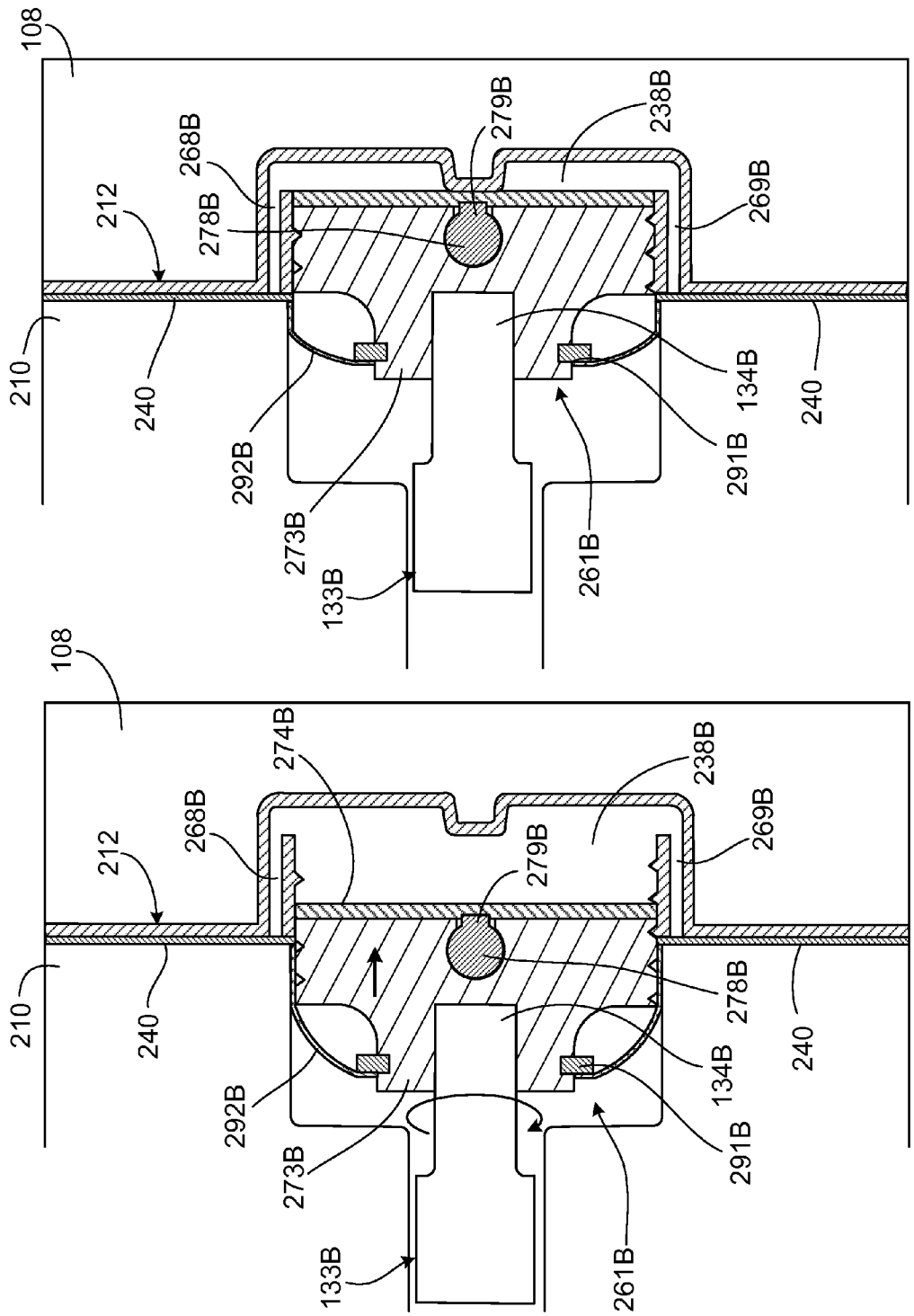

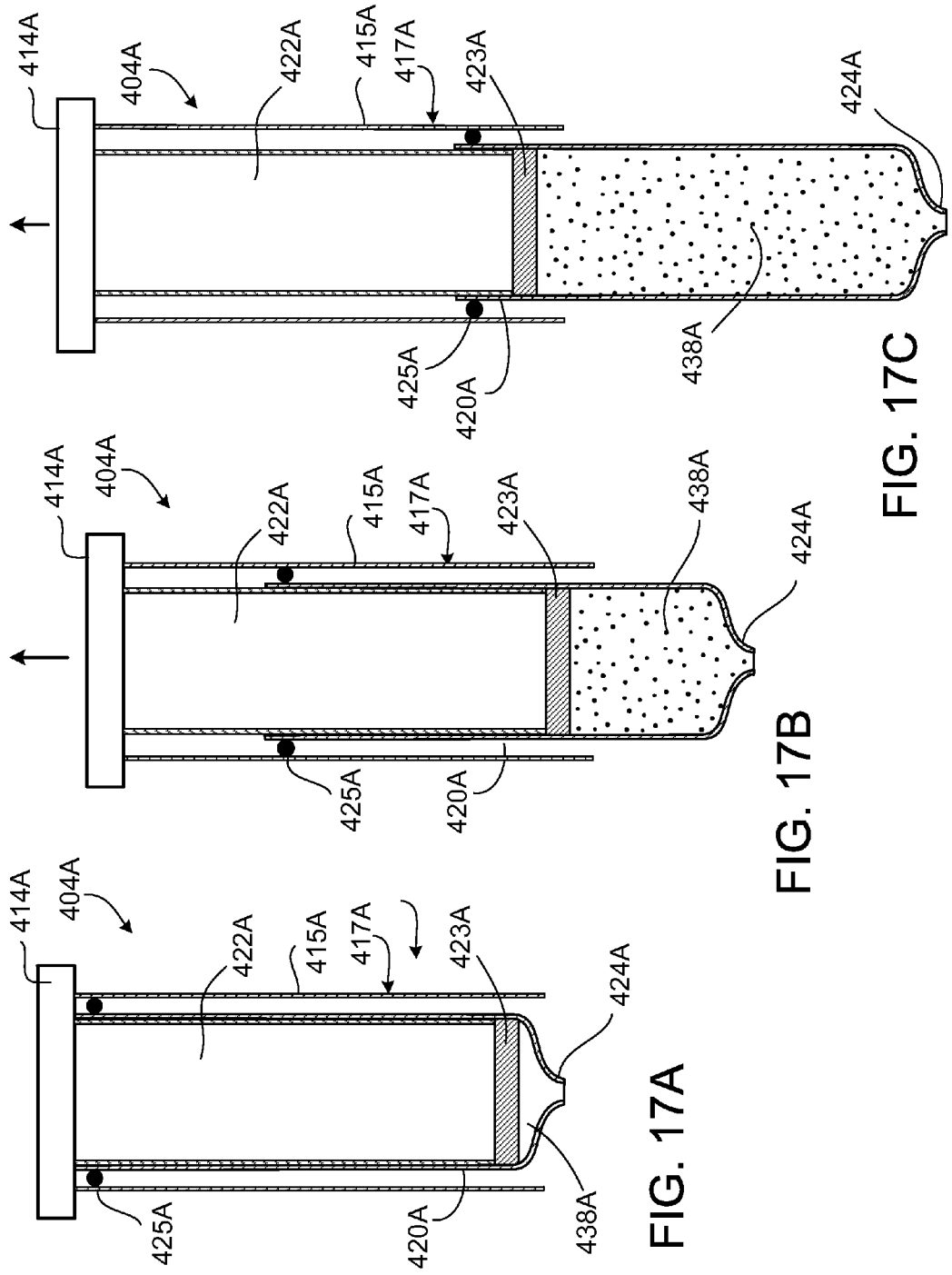

MEDICAL FLUID DELIVERY SETS AND RELATED SYSTEMS AND METHODS

CROSS-REFERENCE TO RELATED APPLICATIONS

This application claims the benefit of U.S. Provisional Application No. 61/450,887, filed on Mar. 9, 2011, which is incorporated by reference herein.

TECHNICAL FIELD

This disclosure relates to medical fluid delivery sets and related systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semipermeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect of the invention, a medical fluid pumping system includes a medical fluid pumping machine defining a cassette enclosure and a medical fluid cassette configured to be disposed within the cassette enclosure of the medical fluid pumping machine. The medical fluid pumping machine includes an actuator. The medical fluid cassette includes a base defining a recess and a plunger slidably disposed within the recess of the base such that a substantially liquid-tight seal is maintained between the plunger and the base as the plunger slides axially within the recess. The plunger and the base cooperate to at least partially define a fluid pump chamber. When the medical fluid cassette is disposed within the cassette enclosure of the medical fluid pumping machine, the actuator can be operated to axially displace the plunger within the recessed region of the base to force fluid out of the fluid pump chamber and to draw fluid into the fluid pump chamber.

In another aspect of the invention, a medical fluid cassette includes a base defining a recess, a membrane attached to the base to form fluid passageways between the membrane and the base, and a plunger slidably disposed within the recess of the base such that a substantially liquid-tight seal is maintained between the plunger and the base as the plunger slides axially within the recess. The plunger and the base cooperate to at least partially define a fluid pump chamber. When the plunger is displaced in a first direction, fluid is forced out of the fluid pump chamber, and when the plunger is displaced in a second direction, fluid is drawn into the fluid pump chamber.

In an additional aspect of the invention, a medical fluid delivery method includes sliding a plunger in a first direction within a recess defined by a base of a medical fluid cassette to draw a medical fluid into a fluid pump chamber formed between the plunger and the base, sliding the plunger in a second direction within the recess to force the medical fluid out of the fluid pump chamber, and occluding a passageway formed between a membrane of the medical fluid cassette and the base of the medical fluid cassette to control flow of the medical fluid within the medical fluid cassette.

In a further aspect of the invention, a medical fluid pumping system includes a medical fluid pumping machine including a drive mechanism and a medical fluid delivery set including a syringe that can be operatively connected to the drive mechanism. The syringe includes a medical fluid containment cylinder and a plunger assembly that can be axially moved relative to the medical fluid containment cylinder. The plunger assembly includes an inner plunger shaft including a seal that is slidably disposed within the medical fluid containment cylinder such that a substantially liquid-tight seal is maintained between the seal of the inner plunger shaft and an inner surface of the medical fluid containment cylinder as the plunger slides axially within the medical fluid containment cylinder. The seal of the shaft plunger and the medical fluid containment cylinder cooperate to at least partially define a fluid pump chamber. The plunger assembly also includes an outer plunger shaft that at least partially surrounds the inner plunger shaft to form a space between an outer surface of the inner plunger shaft and an inner surface of the outer plunger shaft. The space is sized to receive a wall of the medical fluid containment cylinder therein. When the syringe of the medical fluid delivery set is operatively engaged with the drive mechanism, the drive mechanism can be operated to axially displace the plunger shaft assembly relative to the medical fluid containment cylinder to force fluid out of the fluid pump chamber and to draw fluid into the fluid pump chamber.

In another aspect of the invention, a medical fluid delivery set includes a syringe connected to a series of interconnected fluid lines. The syringe includes a medical fluid containment cylinder and a plunger assembly that can be axially moved relative to the medical fluid containment cylinder. The plunger assembly includes an inner plunger shaft including a seal that is slidably disposed within the medical fluid containment cylinder such that a substantially liquid-tight seal is maintained between the seal of the inner plunger shaft and an inner surface of the medical fluid containment cylinder as the plunger slides axially within the medical fluid containment cylinder. The seal of the shaft plunger and the medical fluid containment cylinder cooperate to at least partially define a fluid pump chamber. The plunger assembly also includes an outer plunger shaft that at least partially surrounds the inner plunger shaft to form a space between an outer surface of the inner plunger shaft and an inner surface of the outer plunger shaft. The space is sized to receive a wall of the medical fluid containment cylinder therein.

In an additional aspect of the invention, a medical fluid delivery method includes moving a plunger shaft assembly relative to a medical fluid containment cylinder such that an inner plunger shaft of the plunger shaft assembly travels within the medical fluid containment cylinder and an outer plunger shaft of the plunger shaft assembly travels along an outer surface of the medical fluid containment cylinder. The movement of the plunger shaft assembly causes a medical fluid to be drawn into a fluid pump chamber formed between a seal connected to the inner plunger shaft and an inner surface of the fluid containment cylinder. While moving the plunger shaft assembly relative to the medical fluid containment cylinder, a substantially liquid-tight seal is maintained between the outer plunger shaft and the medical fluid containment cylinder.

Implementations can include one or more of the following features.

In some implementations, axially displacing the plunger in a first direction forces fluid out of the fluid pump chamber and axially displacing the plunger in a second direction draws fluid into the fluid pump chamber.

In certain implementations, axially displacing the plunger in the first direction includes displacing the plunger toward a closed end of the recess, and axially displacing the plunger in the second direction include displacing the plunger toward an open end of the recess that is opposite the closed end of the recess.

In some implementations, axially displacing the plunger in the first direction includes displacing the plunger toward a first closed end of the recess, and axially displacing the plunger in the second direction includes displacing the plunger toward a second closed end of the recess that is opposite the first closed end of the recess.

In certain implementations, the plunger includes a rotatable member and a seal connected to the rotatable member in a manner such that rotation of the rotatable member causes axial movement of the seal, and the seal and the base cooperate to form the substantially liquid-tight seal.

In some implementations, the rotatable member includes a plunger head having threads that matingly engage threads of the base to cause axial movement of the plunger head and seal when the plunger head is rotated.

In certain implementations, the seal is connected to the plunger head in a manner such that the plunger head can rotate relative to the seal.

In some implementations, the seal and the plunger head are connected to one another via a ball joint.

In certain implementations, the medical fluid pumping system further includes a member that is connected to the plunger head in a manner such that the plunger head can rotate relative to the member, and a flexible cover connected at one end to the base of the cassette and connected at an opposite end to the member.

In some implementations, the member is a ring that sits at least partially within an annular channel formed in the plunger head.

In certain implementations, the rotatable member includes a shaft that extends through a hole defined in a plunger head, and the rotatable shaft has threads that matingly engage threads of the plunger head to cause axial movement of the plunger head when the shaft is rotated.

In some implementations, the seal includes an o-ring that surrounds the plunger head.

In certain implementations, the plunger head and the recess have non-circular mating shapes, such that the plunger head is substantially prevented from rotating within the recess relative to the base.

In some implementations, the plunger head and the recess are oval-shaped.

In certain implementations, the shaft extends from a first end region of the recess to a second end region of the recess.

In some implementations, an end region of the shaft is disposed within a blind bore defined in the base adjacent the second end region of the recess.

In certain implementations, the base defines a fluid outlet port through which fluid forced out of the pump chamber passes.

In some implementations, the base further defines a fluid inlet port through which fluid drawn into the pump chamber passes.

In certain implementations, the recess has a first end region and a second end region, the second end region being axially spaced from the actuator by a greater distance than the first end region is axially spaced from the actuator when the actuator is beginning a stroke to force the fluid out of the fluid pump chamber, and the fluid inlet port and the fluid outlet port are defined in a portion of the base that defines the first end region of the recess.

In some implementations, the medical fluid cassette includes a membrane attached to the base.

In certain implementations, the membrane forms an opening that overlies the recess of the base.

In some implementations, the membrane is attached to an annular portion of the base surrounding the recess.

In certain implementations, the medical fluid cassette includes a cap that overlies the recess and is attached to the base.

In some implementations, the cap defines a hole configured to receive a shaft of the plunger.

In certain implementations, the medical fluid pumping system further includes an o-ring positioned between the cap and the shaft of the plunger to form a liquid-tight seal between the cap and the shaft of the plunger.

In some implementations, the actuator includes a rotatable member, and the plunger defines a recess configured to matingly engage the rotatable member.

In certain implementations, the rotatable member includes a hexagonal key, and the recess is hexagonal to matingly engage the hexagonal key.

In some implementations, the medical fluid pumping machine further includes a motor connected to the actuator to drive the actuator.

In certain implementations, the motor is a rotary motor connected to the actuator in a manner such that the actuator is rotated when the rotary motor is operated.

In some implementations, the actuator is connected to the plunger in a manner to rotate the plunger when the actuator is rotated.

In certain implementations, the plunger is connected to the base in a manner such that the plunger is axially displaced within the recess of the base when the actuator is rotated.

In some implementations, the plunger includes a head and a seal connected to the head, and the seal forms the fluid-tight seal with the base.

In certain implementations, the seal is connected to the head in a manner such that the head can rotate relative to the seal.

In some implementations, the seal and the plunger are connected via a ball and socket joint.

In certain implementations, the plunger includes a central threaded shaft extending from a top region of the recess to a bottom region of the recess and a head that is threadedly connected to the central shaft.

In some implementations, the plunger further includes an o-ring secured to the head, and adjacent surfaces of the o-ring and the base form the substantially liquid-tight seal.

In certain implementations, the head is substantially rotationally fixed within the recess such that rotation of the central shaft causes axial displacement of the piston within the recess.

In some implementations, the central shaft mates with the actuator, and the actuator rotates the central shaft.

In certain implementations, the central shaft defines a recess that matingly engages the actuator.

In some implementations, rotation of the central shaft in a first rotational direction causes axial displacement of the head in a first axial direction, and rotation of the central shaft in a second rotational direction causes axial displacement of the head in a second axial direction.

In certain implementations, the base includes a cylindrical wall that defines the recess, and the plunger includes a central plunger shaft disposed within the recess and a cylindrical member that surrounds the central plunger shaft and the cylindrical wall of the base.

In some implementations, the plunger further includes a seal attached to the central plunger shaft, and the seal cooperates with the cylindrical wall of the base to form the substantially liquid-tight seal.

In certain implementations, the cylindrical member of the plunger cooperates with the cylindrical wall of the base to form a substantially liquid-tight seal.

In some implementations, the medical fluid pumping system further includes an o-ring disposed between the cylindrical member of the plunger and the cylindrical wall of the base, and the o-ring cooperates with the cylindrical member of the plunger and the cylindrical wall of the base to form a substantially liquid-tight seal.

In certain implementations, the medical fluid pumping machine is a dialysis machine (e.g., a peritoneal dialysis machine).

In some implementations, the syringe further includes an o-ring positioned between the outer plunger shaft and the medical fluid containment cylinder to create a liquid-tight seal therebetween.

In certain implementations, the medical fluid delivery set further includes a series of interconnected fluid lines.

In some implementations, at least one line of the series of interconnected lines is connected to a port of the medical fluid containment cylinder that is in fluid communication with the fluid pump chamber.

In certain implementations, the medical fluid pumping machine further includes multiple valves, each of which is configured to occlude a portion of one of the fluid lines when activated.

In some implementations, the fluid pump chamber has a volumetric capacity of at least 200 cubic centimeters.

In certain implementations, the medical fluid delivery cassette further includes a second syringe.

In some implementations, the medical fluid pumping machine further includes a second drive mechanism that can operatively engaged the second syringe in a manner to axially displace a plunger shaft assembly of the second syringe relative to a medical fluid containment cylinder of the second syringe to force fluid out of a fluid pump chamber of the second syringe and to draw fluid into the fluid pump chamber of the second syringe.

Implementations can include one or more of the following advantages.

In some implementations, the plunger is configured to convert rotational motion applied to it by the actuator into translational motion within the recess of the base in order to draw fluid into the fluid pump chamber and/or force fluid out of the fluid pump chamber. This arrangement permits precise control of the translational movement and thus increased pumping volume accuracy. At the same time, this arrangement allows for the use of relatively inexpensive actuators and can thus reduce the overall manufacturing cost of the system.

In certain implementations, the plunger includes a head and a seal that is connected to the head in a manner such that the head can be rotated relative to the seal. The head is typically connected (e.g., threadedly connected) to the base of the cassette in a manner such that rotation of the head causes translational motion of the base and the seal. Because the head is allowed to rotate relative to the seal, the movement of the seal within the recess of the base can be restricted to substantially only translational movement. This can help to reduce wear and tear on the seal during use and can thus help to prevent leaking of fluid between the seal and the surrounding base during use.

In some implementations, the recess in the base has a non-circular shape (e.g., an oval shape) and a head of the plunger has a mating non-circular shape. In such implementations, rotation of the plunger head within the recess can be inhibited (e.g., prevented). This can allow rotational motion of a shaft or other member that is threadedly connected to the plunger head to be converted into translational motion of the plunger head within the recess.

In certain implementations, the medical fluid cassette includes a membrane with an opening such that the actuator of the fluid pumping machine can directly contact the plunger of the cassette. Because the actuator transmits motion only to the plunger and not the membrane, the resistance encountered by the actuator is more consistent throughout the stroke of the plunger than the resistance encountered by the actuator of certain systems that utilize the actuator to deform a membrane into a recess in a base as part of a fluid pumping action. Thus, the pumping volume accuracy of the system can be increased relative to many of those systems that utilize the actuator to deform a membrane into a recess in a base as part of a fluid pumping action.

In some implementations, the fluid pump chamber of the cassette has a substantially constant cross-sectional area along its length, and the volume of the fluid pump chamber is increased and decreased by translating the plunger within the fluid pump chamber, which causes fluid to be drawn into or forced out of the fluid pump chamber. As a result, the volume of fluid drawn into and forced out of the fluid pump chamber can typically be determined by simply multiplying the distance of travel of the plunger by the cross-sectional area of the fluid pump chamber. Consequently, relatively basic and inexpensive processors can be used in many cases to determine the pumped fluid volume.

In many implementations, a relatively simple mechanical connection, such as a key/recess connection, can be used to connect the actuator of the medical fluid pumping machine to the plunger of the medical fluid cassette. As a result, the system can be more user-friendly, less expensive, and quieter than certain medical fluid pumping systems that utilize vacuum-based connections between a medical fluid pumping machine and a medical fluid cassette.

In some implementations, a fluid port (e.g., a fluid inlet port, a fluid outlet port, or both) can be located in an end region of the recess that is nearest the actuator of the medical fluid pumping machine, and the plunger is configured so that movement of the plunger away from the actuator (or away from the surface of the medical fluid pumping machine from which the actuator extends) draws fluid into the fluid pump chamber and movement of the plunger toward the actuator (or toward the surface of the medical fluid pumping machine from which the actuator extends) forces fluid out of the fluid pump chamber. Thus, the fluid port can be in substantially the same plane as various fluid paths formed in the cassette. This arrangement can simplify the fluid path from the fluid pump chamber to fluid passageways in the cassette and, in some cases, can reduce the overall depth of the portion of the cassette forming the fluid pump chamber as compared to cassettes that include such a fluid port in the opposite end region of the recess that forms the fluid pump chamber.

In certain implementations, the portions of the plunger that contact the outside environment during use are isolated from those portions of the plunger that contact the medical fluid during use. This can reduce (e.g., minimize) the risk of contamination of the medical fluid by the surrounding environment.

Other aspects, features, and advantages will be apparent from the description and drawings, and from the claims.

DESCRIPTION OF DRAWINGS

FIGS. 9A-9C are diagrammatic cross-sectional views of the PD cassette in the cassette compartment of the PD cycler of the PD system of FIG. 1, during different phases of a pumping operation.

FIGS. 13A-13C are diagrammatic cross-sectional views of the PD cassette of FIG. 10 in the cassette compartment of a PD cycler, during different phases of a pumping operation.

FIGS. 17A-17C are diagrammatic cross-sectional views of the syringe of FIG. 16 during different phases of a PD solution delivery process during which PD solution is drawn into the syringe and then expelled from the syringe.

DETAILED DESCRIPTION

This disclosure relates generally to medical fluid delivery sets and related systems and methods. In certain aspects of the invention, a medical fluid cassette (e.g., a peritoneal dialysis ("PD") fluid cassette) includes a plunger that is slidably disposed within a recess formed in a base of the cassette. During use, an actuator of a medical fluid pumping machine (e.g., a PD cycler) applies a force to the plunger that causes translational motion of a seal of the plunger within the recess thereby decreasing the volume of a fluid pump chamber formed between the plunger seal and the base and forcing fluid out of the fluid pump chamber. The actuator subsequently applies an opposite force to the plunger, which causes translational motion of the plunger seal in an opposite direction within the recess. This motion increases the volume of the fluid pump chamber causing fluid to be drawn into the fluid pump chamber. Examples of various different medical fluid sets and medical fluid pumping machines are described below.

Figure 1:
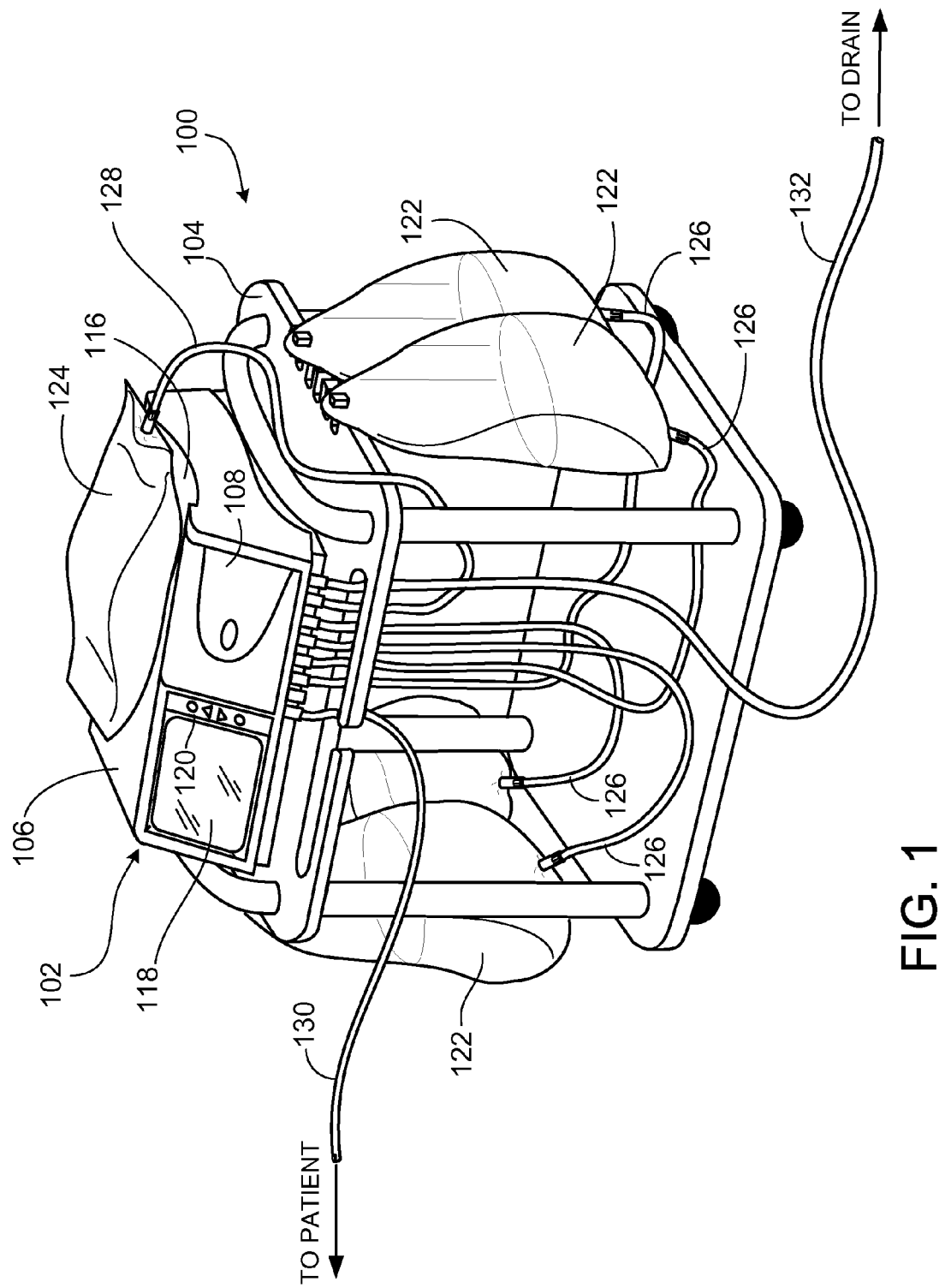
FIG. 1 is a perspective view of a peritoneal dialysis ("PD") system that includes a PD cycler positioned atop a portable cart.
Figure 2:
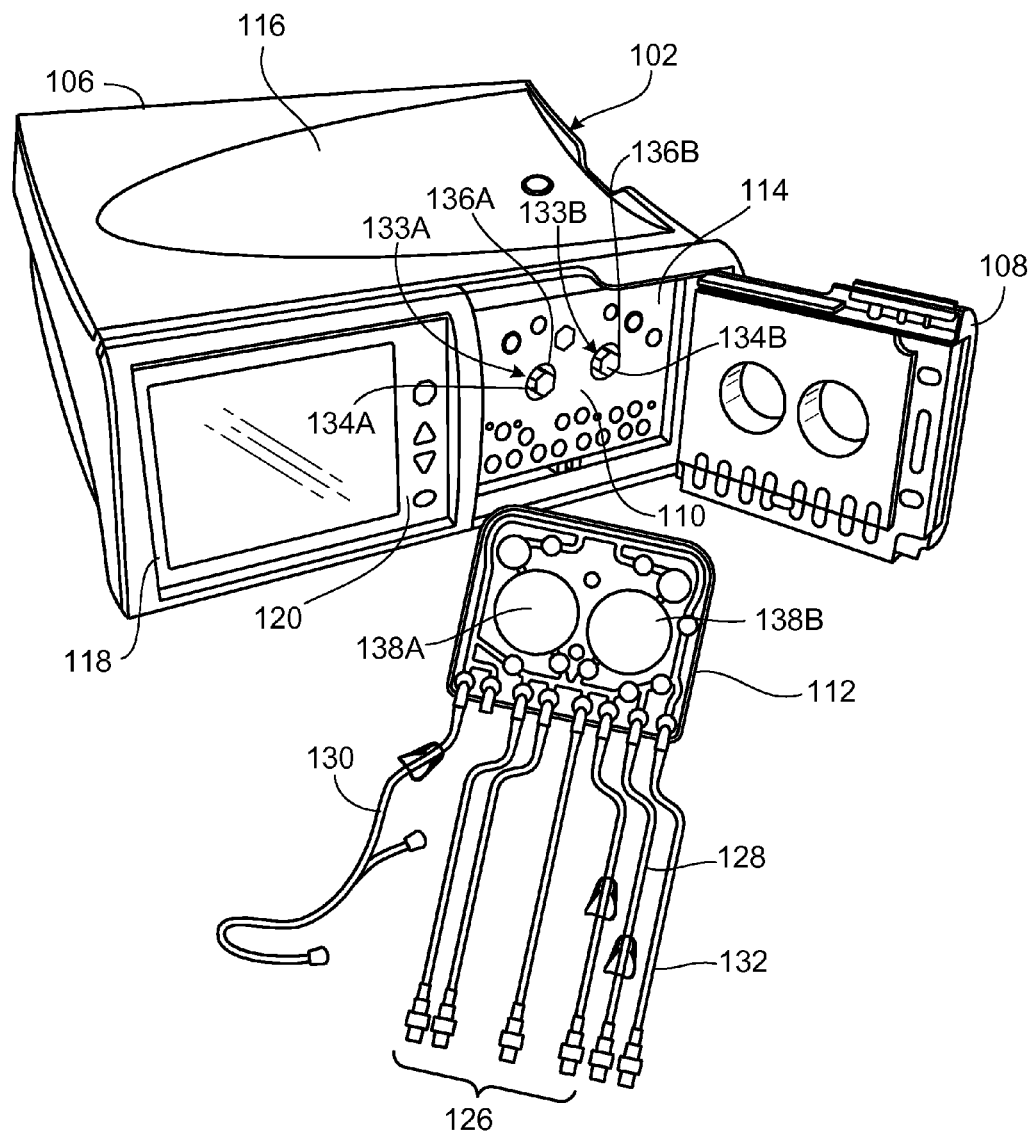
FIG. 2 is a perspective view of the PD cycler and PD cassette of the PD system of FIG. 1. A door of the PD cycler is in the open position to show the inner surfaces of the PD cycler that interface with the PD cassette during use.

Referring to FIG. 1, a PD system 100 includes a PD cycler (also referred to as a PD machine) 102 seated on a cart 104. Referring also to FIG. 2, the PD cycler 102 includes a housing 106, a door 108, and a cassette interface 110 that abuts a disposable PD cassette 112 when the cassette 112 is disposed within a cassette compartment 114 formed between the cassette interface 110 and the closed door 108. A heater tray 116 is positioned on top of the housing 106. The heater tray 116 is sized and shaped to accommodate a bag of dialysis solution (e.g., a 5 liter bag of dialysis solution). The PD cycler 102 also includes a touch screen 118 and additional control buttons 120 that can be operated by a user (e.g., a patient) to allow, for example, set-up, initiation, and/or termination of a PD treatment.

Dialysis solution bags 122 are suspended from fingers on the sides of the cart 104, and a heater bag 124 is positioned on the heater tray 116. The dialysis solution bags 122 and the heater bag 124 are connected to the cassette 112 via dialysis solution bag lines 126 and a heater bag line 128, respectively. The dialysis solution bag lines 126 can be used to pass dialysis solution from dialysis solution bags 122 to the cassette 112 during use, and the heater bag line 128 can be used to pass dialysis solution back and forth between the cassette 112 and the heater bag 124 during use. In addition, a patient line 130 and a drain line 132 are connected to the cassette 112. The patient line 130 can be connected to a patient's abdomen via a catheter and can be used to pass dialysis solution back and forth between the cassette 112 and the patient during use. The drain line 132 can be connected to a drain or drain receptacle and can be used to pass dialysis solution from the cassette 112 to the drain or drain receptacle during use.

Figure 3:
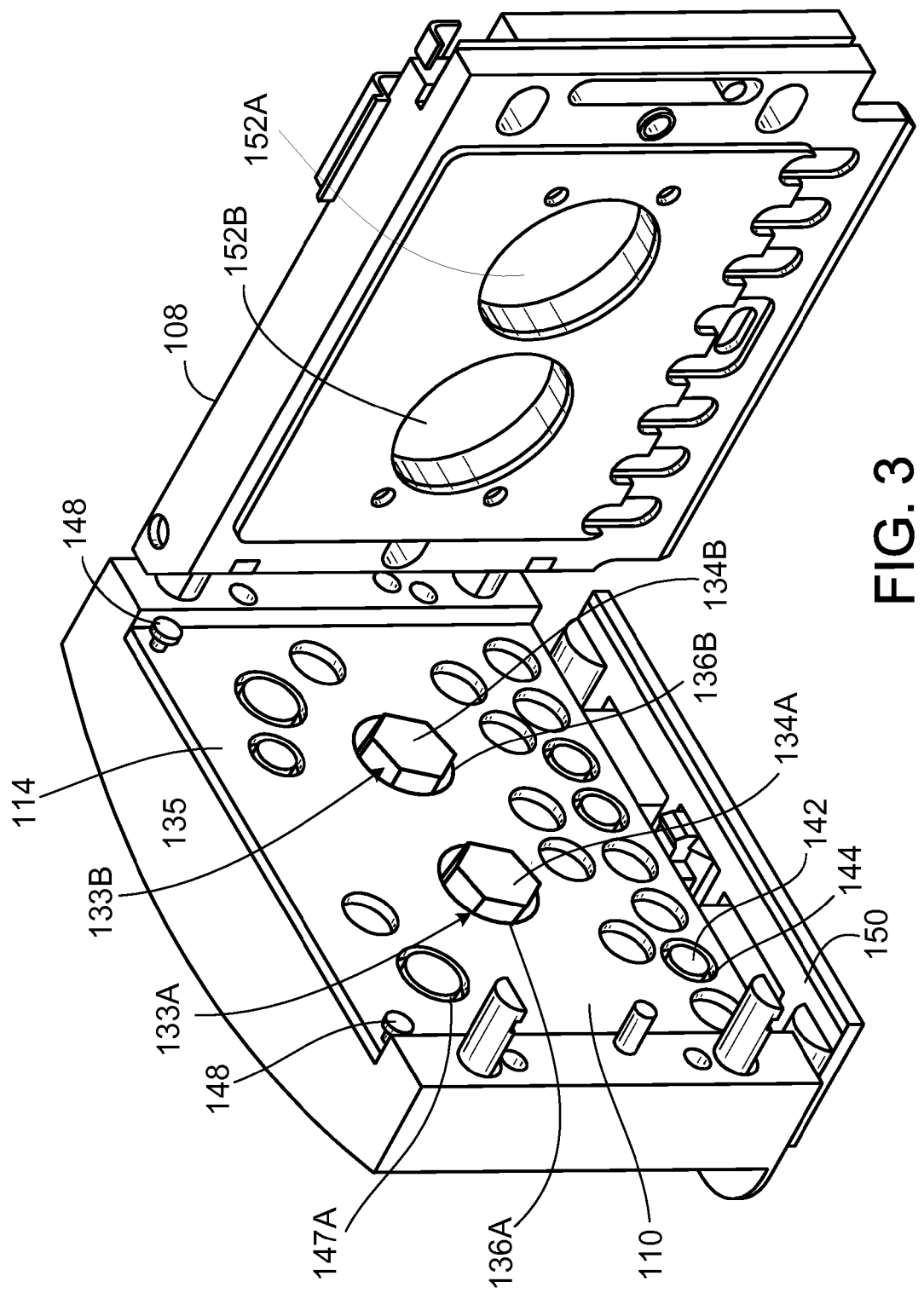
FIG. 3 is a perspective view of an open cassette compartment of the PD cycler of FIGS. 1 and 2, showing, among other things, rotatable actuators of the PD cycler.

FIG. 3 shows a more detailed view of the cassette interface 110 and the door 108 of the PD cycler 102. As shown, the PD cycler 102 includes actuators 133A, 133B having hexagonal keys 134A, 134B disposed within ports 136A, 136B formed in the cassette interface 110. The hexagonal keys 134A, 134B are attached to rotatable shafts 143A, 143B (shown in FIGS. 9A-9C below) of the actuators 133A, 133B. The rotatable shafts 143A, 143B are connected to electromechanical motors (e.g., DC motors, brushless DC motors, stepper motors), typically contained within the housing 106 of the PD cycler 102, that can rotate the shafts 143A, 143B and the hexagonal keys 134A, 134B.

When the cassette 112 (shown in FIGS. 2 and 4-8) is loaded in the cassette compartment 114 between the cassette interface 110 and the door 108 of the PD cycler 102, the hexagonal keys 134A, 134B of the actuators 133A, 133B matingly engage hexagonal recesses 175A, 175B formed in plungers 161A, 161B of the cassette 112. Rotational motion of the hexagonal keys 134A, 134B during use imparts a rotational force to the plungers 161A, 161B and, due to the construction of the plungers 161A, 161B and the base 156 of the cassette 112, that rotational force is converted to translational motion of seals of the plungers 161A, 161B. This translational motion of the seals of plungers 161A, 161B is used to draw PD solution into and force PD solution out of fluid pump chambers 138A, 138B of the cassette 112, as will be described in greater detail below.

The actuators 133A, 133B, including the hexagonal keys 134A, 134B and the rotatable shafts 143A, 143B, are typically formed of one or more metals, such as stainless steel and/or aluminum. However, the hexagonal keys 134A, 134B and the rotatable shafts 143A, 143B can alternatively be formed of one or more relatively rigid polymers, such as polyetherimides (e.g., Ultem® polyetherimide) and/or polyphenylenesulphides (e.g., Ryton® polyphenylenesulphides). The actuators 133A, 133B can be formed using any of various different techniques, including machining techniques molding techniques, and/or casting techniques.

Referring again to FIG. 3, the PD cycler 102 also includes multiple inflatable members 142 positioned within inflatable member ports 144 in the cassette interface 110. The inflatable members 142 align with depressible dome regions 146 of the cassette 112 when the cassette 112 is positioned within the cassette compartment 114 of the PD cycler 102. While only one of the inflatable members 142 is labeled in FIG. 3, it should be understood that the PD cycler 102 includes an inflatable member associated with each of the depressible dome regions 146 of the cassette 112 (shown in FIG. 6). The inflatable members 142 act as valves to direct dialysis solution through the cassette 112 in a desired manner during use. In particular, the inflatable members 142 bulge outward beyond the surface of the cassette interface 110 and into contact with the depressible dome regions 146 of the cassette 112 when inflated, and retract into the inflatable member ports 144 and out of contact with the cassette 112 when deflated. By inflating certain inflatable members 142 to depress their associated dome regions 146 on the cassette 112, certain fluid flow paths within the cassette 112 can be occluded. Thus, PD solution can be pumped through the cassette 112 by actuating the piston heads 134A, 134B, and can be guided along desired flow paths within the cassette 112 by selectively inflating and deflating the inflatable members 142.

Still referring to FIG. 3, locating pins 148 extend from the cassette interface 110. When the door 108 is in the open position, the cassette 112 can be loaded onto the cassette interface 110 by positioning the top portion of the cassette 112 under the locating pins 148 and pushing the bottom portion of the cassette 112 toward the cassette interface 110. The cassette 112 is dimensioned to remain securely positioned between the locating pins 148 and a lower ledge 150 extending from the cassette interface 110 to allow the door 108 to be closed over the cassette 112. The locating pins 148 help to ensure that the hexagonal recesses 175A, 175B in the plungers 161A, 161B of the cassette 112 are aligned with the hexagonal keys 134A, 134B of the actuators 133A, 133B when the cassette 112 is positioned in the cassette compartment 114. The locating pins 148 can also help to ensure that proper alignment of the cassette 112 within the cassette compartment 114 is maintained during use.

The door 108 of the PD cycler 102, as shown in FIG. 3, defines cylindrical recesses 152A, 152B that substantially align with the actuators 133A, 133B when the door 108 is in the closed position. When the cassette 112 is positioned within the cassette compartment 114, hollow projections 154A, 154B of the cassette 112 (shown in FIGS. 7 and 8), inner surfaces of which cooperate with the seals of the plungers 161A, 161B to form the pump chambers 138A, 138B, fit within the recesses 152A, 152B. The door 108 further includes a pad that is inflated during use to compress the cassette 112 between the door 108 and the cassette interface 110. With the pad inflated, the portions of the door 108 forming the recesses 152A, 152B support the projections 154A, 154B of the cassette 112 and the planar surface of the door 108 supports the other regions of the cassette 112. The door 108 can counteract the forces applied by the inflatable members 142 and thus allows the inflatable members 142 to actuate the depressible dome regions 146 on the cassette 112. The engagement between the door 108 and the hollow projections 154A, 154B of the cassette 112 can also help to hold the cassette 112 in a desired fixed position within the cassette compartment 114 to further ensure that the plungers 161A, 161B align with the fluid pump chambers 138A, 138B of the cassette 112.

Figure 4:
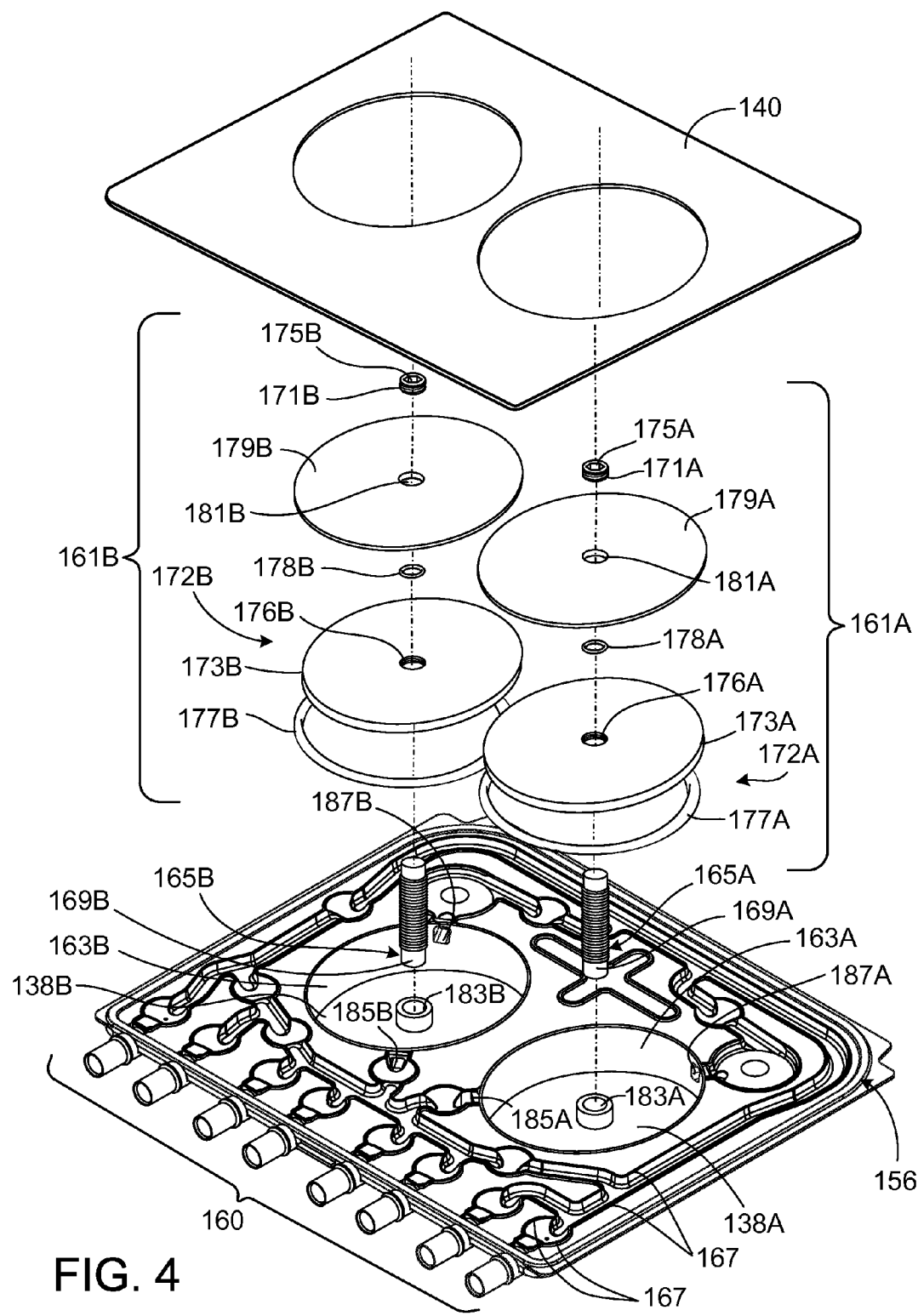
FIG. 4 is an exploded, perspective view of the PD cassette of the PD system of FIG. 1, which includes a plunger slidably disposed within a chamber of the cassette.
Figure 5:
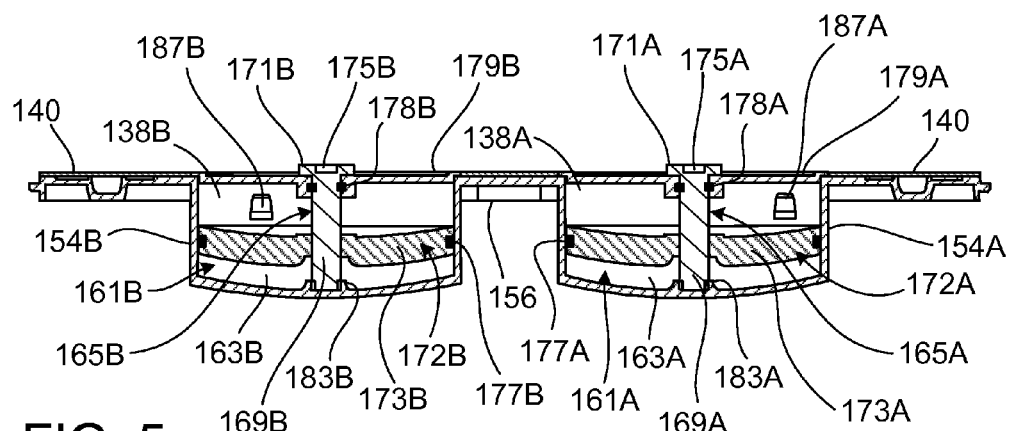
FIG. 5 is a cross-sectional view of the PD cassette of FIG. 4 when fully assembled.
Figure 6:
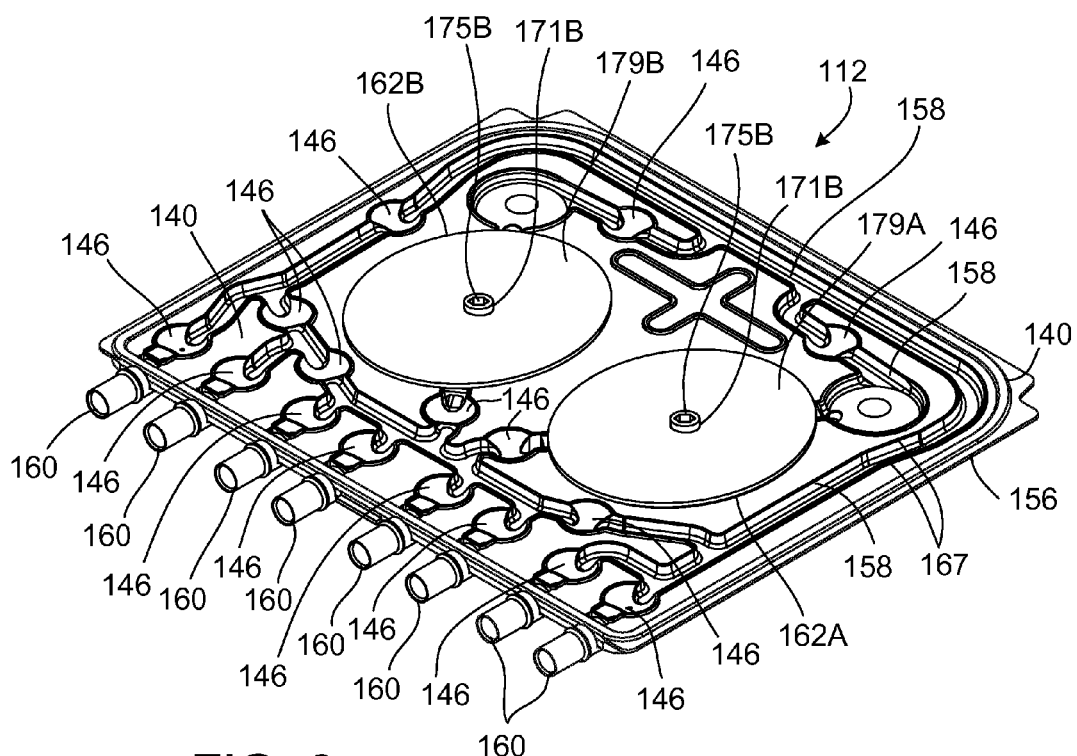
FIG. 6 is a perspective view of the PD cassette of FIG. 4, from a flexible membrane side of the PD cassette.
Figure 7:
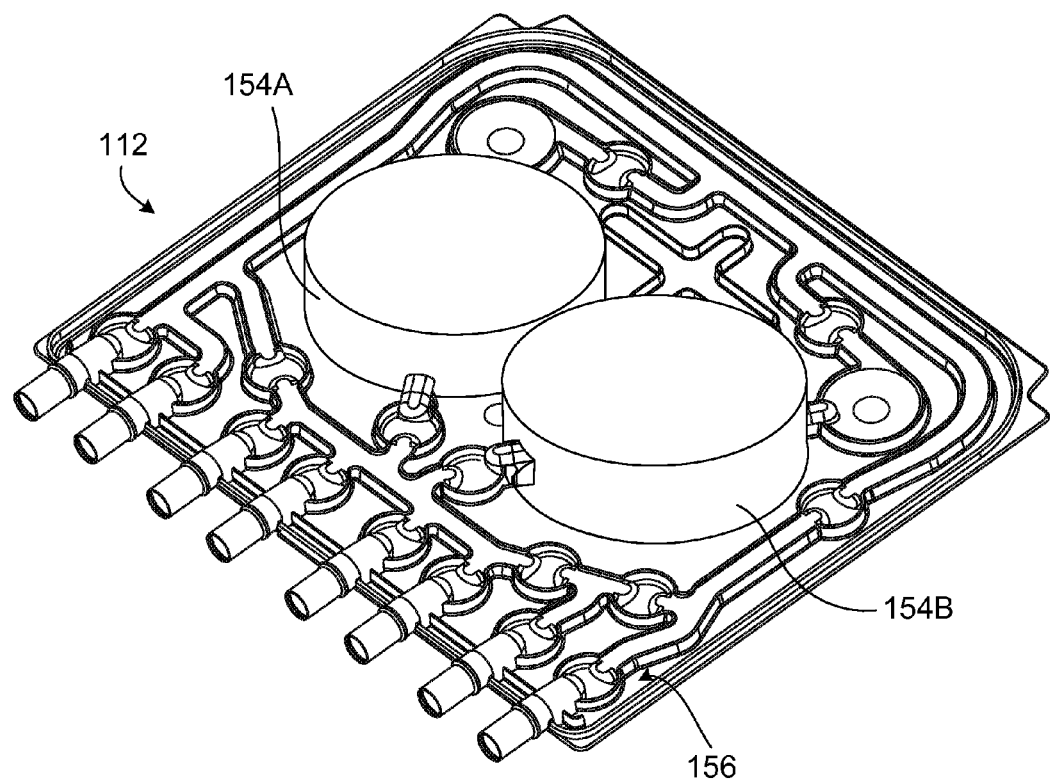
FIG. 7 is a perspective view of the PD cassette of FIG. 4, from a rigid base side of the PD cassette.

FIG. 4 is an exploded, perspective view of the cassette 112, FIG. 5 is a perspective, cut-away view of the fully assembled cassette 112, and FIGS. 6 and 7 are perspective views of the assembled cassette 112, from the membrane side and from the rigid base side, respectively. Referring to FIGS. 4-7, the cassette 112 includes a flexible membrane 140 attached to the tray-like rigid base 156. More specifically, the flexible membrane 140 is attached to the periphery of the base 156 and to regions of the base 156 surrounding oval-shaped recessed regions 163A, 163B formed by the hollow projections 154A, 154B of the base 156. Oval-shaped caps 179A, 179B are also attached to regions of the base 156 surrounding the recessed regions 163A, 163B in a manner such that the caps 179A, 179B cover the recessed regions 163A, 163B of the base 156 and the plungers 161A, 161B, which are slidably disposed in the recessed regions 163A, 163B of the base 156. Raised ridges 167 extend from the planar surface of the base 156 towards and into contact with the inner surface of the flexible membrane 140 when the cassette 112 is compressed between the door 108 and the cassette interface 110 of the PD cycler 102 to form a series of fluid passageways in the cassette 112 that fluidly connect the inlet/outlet ports 160 of the cassette 112 to the fluid pump chambers 138A, 138B.

Still referring to FIGS. 4-7, each of the plungers 161A, 161B includes a screw 165A, 165B onto which an oval disk 173A, 173B is threaded. The screw 165A, 165B of each plunger 161A, 161B includes a threaded shaft 169A, 169B and an enlarged head 171A, 171B attached to one end of the shaft 169A, 169B. The hexagonal recess 175A, 175B is formed in the enlarged head 171A, 171B and is sized and shaped to receive and matingly engage the hexagonal key 134A, 134B of the actuator 133A, 133B of the PD cycler 102 (shown in FIGS. 1-3). The opposite end region of the shaft 169A, 169B, which is unthreaded, is disposed in a cavity formed by an annular protrusion 183A, 183B extending upward from a bottom surface (as viewed in FIG. 4) of the recessed region 163A, 163B of the base 156. The shaft 169A, 169B is allowed to freely rotate within the cavity of the annular protrusions 183A, 183B. At the same time, the annular protrusion 183A, 183B helps to keep the screw 165A, 165B positioned along the central axis of the recessed region 163A, 163B formed in the base 156, which can help to ensure that the oval disk 173A, 173B of each plunger 161A, 161B remains substantially parallel to the bottom surface of the recessed region 163A, 163B of the base 156 and to the oval cap 179A, 179B.

The oval-shaped disk 173A, 173B of each of the plungers 161A, 161B has a threaded central bore 176A, 176B that receives the threaded shaft 169A, 169B of the associated screw 165A, 165B. The threads of the shaft 169A, 169B matingly engage the threads along the bore 176A, 176B in the oval-shaped disk 173A, 173B such that the oval-shaped disk 173A, 173B can be translated along the length of the shaft 169A, 169B when the shaft 169A, 169B is rotated relative to the oval-shaped disk 173A, 173B. Each plunger 161A, 161B also includes a resilient o-ring 177A, 177B that surrounds the oval-shaped disk 173A, 173B and provides a liquid-tight seal with the inner surface of the hollow protrusion 154A, 154B of the base 156 of the cassette 112.

The oval caps 179A, 179B, which are attached to the portions of the base 156 surrounding the oval-shaped recessed regions 163A, 163B, include central bores 181A, 181B in which unthreaded top regions (from the perspective of FIGS. 4 and 5) of the screw shafts 169A, 169B are disposed. O-rings 178A, 178B are positioned in the bores 181A, 181B and surround the screw shafts 169A, 169B. The o-rings 178A, 178B are secured within annular depressions formed in the oval caps 179A, 179B to limit (e.g., prevent) axial movement of the o-rings relative to the oval caps 179A, 179B as the screw shafts 169A, 169B translate axially. As a result of this arrangement, the shafts 169A, 169B are able to rotate within the bores 181A, 181B of the fixed caps 179A, 179B while a liquid-tight seal is provided by the o-rings 178A, 178B. Alternatively or additionally, other techniques, such as adhesive bonding or thermal bonding, can be used to secure the o-rings 178A, 178B to the oval caps 179A, 179B.

The fluid pump chamber 138B and the general operation of the plunger 161B will now be described with reference to FIG. 5. It should be appreciated that the other fluid pump chamber 138A and plunger 161A have substantially the same structure and function as the fluid pump chamber 138B and plunger 161B to be described. As shown in FIG. 5, the fluid pump chamber 138B is formed between the plunger head assembly 172B (i.e., the assembly of the oval disk 173B and the o-ring 177B) and the oval cap 179B. The engagement between the o-ring 177B and the inner side wall of the hollow protrusion 154B, which forms the recessed region 163B, forms a liquid-tight seal to contain liquid within the fluid pump chamber 138B. The o-ring 178B compressed between the oval cap 179B and the outer circumference of the shaft 169B also serves to contain liquid within the fluid pump chamber 138B. When the screw 165B is rotated in a first direction, the plunger head assembly 172B is caused to be translated along the threaded shaft 169B of the screw 165B toward the bottom surface of the recessed region 163B of the base 156. Because the plunger head assembly 172B and the recessed region 163B have mating oval shapes, the plunger head assembly 172B is substantially prevented from rotating within the recessed region 163B. Thus, as the screw 165B is rotated in the first direction, the plunger head assembly 172B is not permitted to rotate with the screw 165B. The relative rotation between the screw 165B and the plunger head assembly 172B in combination with the threaded engagement between those components causes the plunger head assembly 172B to move linearly along the screw 165B, toward the bottom surface of the recessed region 163B of the base 156. Depending on the state of the various inflatable valve members 142 of the PD cycler 102 (shown in FIGS. 2 and 3) that act on the cassette 112 during use, this action can cause liquid to be drawn from a liquid source (e.g., a dialysate bag or a patient's peritoneal cavity) into the fluid pump chamber 138B via an inlet port 185B (shown in FIG. 4) formed in the base 156 of the cassette 156 adjacent a top region (as viewed in FIG. 5) of the fluid pump chamber 138B. For similar reasons, rotation of the screw 165B in a second direction that is opposite the first direction causes the plunger head assembly 172B to move linearly along the screw 165B toward the oval cap 179A of the cassette. Depending on the state of the various valve members of the PD cycler 102 that act on the cassette 112 during use, this action can cause liquid to be forced out of the fluid pump chamber 138B via an outlet port 187B formed in the base 156 of the cassette 156 adjacent a top region (as viewed in FIG. 5) of the fluid pump chamber 138B. The liquid can, for example, be delivered from the fluid pump chamber 138B to a drain bag or to a peritoneal cavity of a patient.

As noted above, the various inflatable valve members 142 of the PD cycler 102 act on the cassette 112 during use. Referring to FIG. 6, when the cassette 112 is compressed between the door 108 and the cassette interface 110 of the PD cycler 102, the membrane 140 cooperates with the series of raised ridges 167 extending from the base 156 to form a series of fluid pathways 158 and to form the multiple, depressible dome regions 146, which are widened portions (e.g., substantially circular widened portions) of the fluid pathways 158. During use, the dialysis solution flows to and from the pump chambers 138A, 138B through the fluid pathways 158 and dome regions 146. At each depressible dome region 146, the membrane 140 can be deflected to contact the planar surface of the base 156 from which the raised ridges 167 extend. Such contact can substantially impede (e.g., prevent) the flow of dialysis solution along the region of the pathway 158 associated with that dome region 146 during use. Thus, the flow of dialysis solution through the cassette 112 can be controlled through the selective depression of the depressible dome regions 146 by selectively inflating the inflatable members 142 of the PD cycler 102.

Referring to FIG. 7, which shows a perspective view of the cassette 112 from the side of the rigid base 156, the recessed regions 163A, 163B (shown in FIG. 4) of the base 156 are formed by the hollow projections 154A, 154B, which extend away from the flexible membrane 140. The hollow projections 154A, 154B are substantially symmetrically positioned with respect to the center vertical axis of the cassette 112. The outer surfaces of the hollow projections 154A, 154B are cylindrical and are sized to fit within the recesses 152A, 152B in the door 108 of the PD cycler 102. The inner surfaces of the hollow projections 154A, 154B form the oval-shaped recessed regions 163A, 163B.

The rigidity of the base 156 helps to hold the cassette 112 in place within the cassette compartment 114 of the PD cycler 102 and to prevent the base 156 from flexing and deforming in response to forces applied to the projections 154A, 154B by the plungers 161A, 161B and in response to forces applied to the planar surface of the base 156 by the inflatable members 142.

The base 156 and the various other components of the cassette 112 except for the o-rings 177A, 177B, 178A, 178B can be formed of any of various relatively rigid materials. In some implementations, these components of the cassette 112 are formed of one or more polymers, such as polypropylene, polyvinyl chloride, polycarbonate, polysulfone, and other medical grade plastic materials. In certain implementations, these components can be formed of one or more metals or alloys, such as stainless steel. These components of can alternatively be formed of various different combinations of the above-noted polymers and metals. These components of the cassette 112 can be formed using any of various different techniques, including machining, molding, and casting techniques.

The o-rings 177A, 177B, 178A, 178B of the cassette 112 are typically formed of one or more resilient materials, such as fluoroelastomer (e.g., Viton® fluoroelastomer), polytetrafluoroethylene (PTFE), and rubber.

Referring again to FIGS. 4 and 6, fluid line connectors 160 are positioned along the bottom edge of the cassette 112. The fluid pathways 158 in the cassette 112 lead from the pumping chambers 138A, 138B to the various connectors 160. The connectors 160 are positioned asymmetrically along the width of the cassette 112. The asymmetrical positioning of the connectors 160 helps to ensure that the cassette 112 will be properly positioned in the cassette compartment 114 with the membrane 140 of the cassette 112 facing the cassette interface 110. The connectors 160 are configured to receive fittings on the ends of the dialysis solution bag lines 126, the heater bag line 128, the patient line 130, and the drain line 132. One end of the fitting can be inserted into and bonded to its respective line and the other end can be inserted into and bonded to its associated connector 160. By permitting the dialysis solution bag lines 126, the heater bag line 128, the patient line 130, and the drain line 132 to be connected to the cassette, as shown in FIGS. 1 and 2, the connectors 160 allow dialysis solution to flow into and out of the cassette 112 during use.

As noted above, the membrane 140 is attached to the periphery of the base 156 and to annular portions of the base surrounding the recessed regions 163A, 163B. The portion of the membrane 140 overlying the remaining of the base 156 are typically not attached to the base 156. Rather, these portions of the membrane 140 sit loosely atop the raised ridges 165A, 165B, and 167 extending from the planar surface of the base 156. Any of various attachment techniques, such as adhesive bonding and thermal bonding, can be used to attach the membrane 140 to the periphery of the base 156. The thickness and material(s) of the membrane 140 are selected so that the membrane 140 has sufficient flexibility to flex toward the base 156 in response to the force applied to the membrane 140 by the inflatable members 142. In certain implementations, the membrane 140 is about 0.100 micron to about 0.150 micron in thickness. However, various other thicknesses may be sufficient depending on the type of material used to form the membrane 140.

Any of various different materials that permit the membrane 140 to deflect in response to movement of the inflatable members 142 without tearing can be used to form the membrane 140. In some implementations, the membrane 140 includes a three-layer laminate. In certain implementations, for example, inner and outer layers of the laminate are formed of a compound that is made up of 60 percent Septon® 8004 thermoplastic rubber (i.e., hydrogenated styrenic block copolymer) and 40 percent ethylene, and a middle layer is formed of a compound that is made up of 25 percent Tuftec® H1062(SEBS: hydrogenated styrenic thermoplastic elastomer), 40 percent Engage® 8003 polyolefin elastomer (ethylene octene copolymer), and 35 percent Septon® 8004 thermoplastic rubber (i.e., hydrogenated styrenic block copolymer). The membrane can alternatively include more or fewer layers and/or can be formed of different materials.

Figure 8:
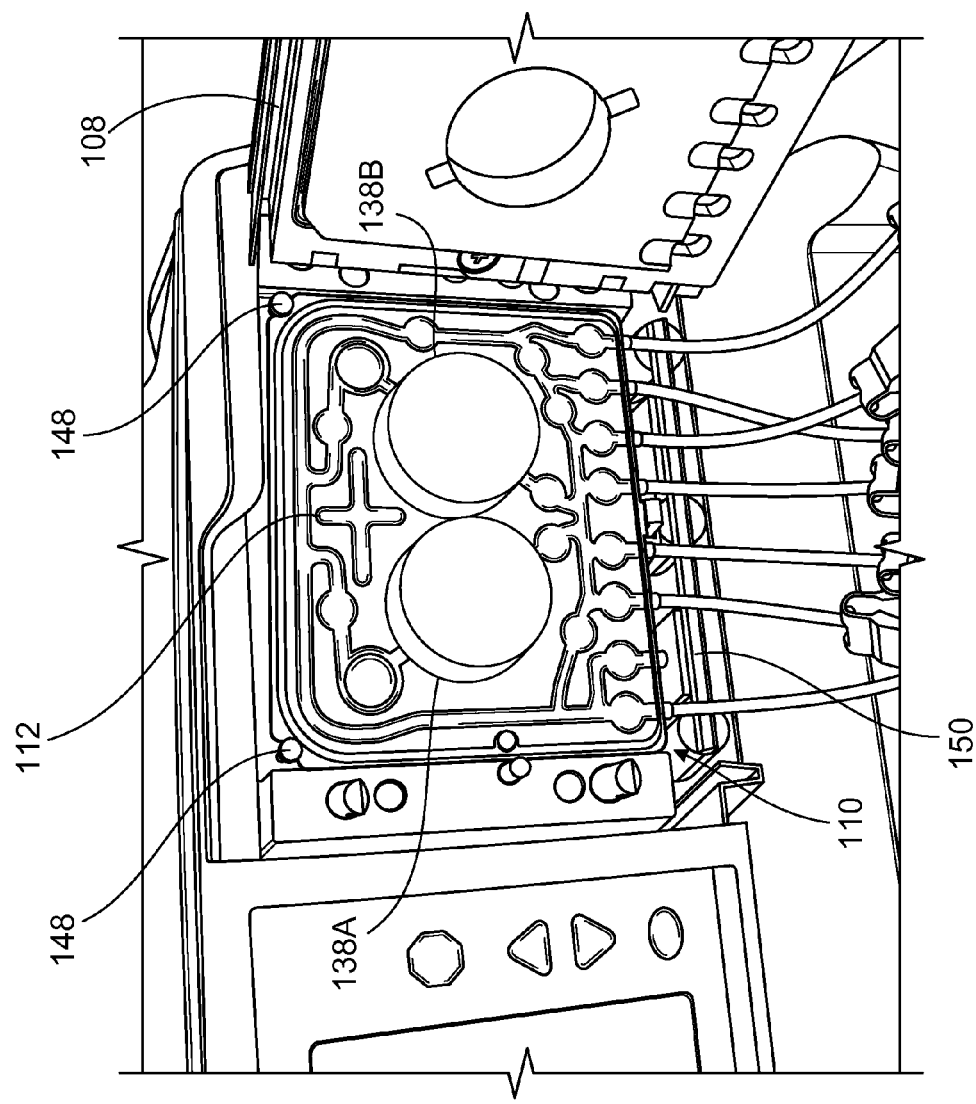
FIG. 8 is a partial perspective view of the PD cassette in the cassette compartment of the PD cycler of the PD system of FIG. 1.

As shown in FIG. 8, before treatment, the door 108 of the PD cycler 102 is opened to expose the cassette interface 110, and the cassette 112 is positioned with its plungers 161A, 161B aligned with the actuators 133A, 133B of the PD cycler 102 and with its membrane 140 adjacent to the cassette interface 110. In order to ensure that the plungers 161A, 161B align with the actuators 133A, 133B, the cassette 112 is positioned between the locating pins 148 and the lower ledge 150 extending from the cassette interface 110. The asymmetrically positioned connectors 160 of the cassette act as a keying feature that reduces the likelihood that the cassette 112 will be installed with the membrane 140 facing in the wrong direction (e.g., facing outward toward the door 108). Additionally or alternatively, the locating pins 148 can be dimensioned to be less than the maximum protrusion of the projections 154A, 154B such that the cassette 112 cannot contact the locating pins 148 if the membrane 140 is facing outward toward the door 108. The hexagonal recesses 175A, 175B of the plunger screws 165A, 165B are aligned with the hexagonal keys 134A, 134B of the actuators 133A, 133B, and the cassette 112 is pressed against the cassette interface 110 such that the hexagonal keys 134A, 134B slide into the hexagonal recesses 175A, 175B.

In certain implementations, the walls of the plunger screws 165A, 165B that form the hexagonal recesses 175A, 175B are tapered inwardly to help properly align the hexagonal keys 134A, 134B with the hexagonal recesses 175A, 175B. In particular, in such implementations, the portions of the hexagonal recesses 175A, 175B that first receive the hexagonal keys 134A, 134B are large enough that the hexagonal keys 134A, 134B can fit into those portions even if the hexagonal keys 134A, 134B are not properly aligned or centered within the recesses 175A, 175B. If the hexagonal keys 134A, 134B are misaligned or off-center, as they are inserted deeper into the recesses 175A, 175B, that condition will correct itself because the cassette 112 will, if necessary, shift slightly to receive the hexagonal keys 134A, 134B, and/or the hexagonal keys 134A, 134B will, if necessary, be rotated slightly to allow them to slide completely into the recesses 175A, 175B.

In some implementations, the actuators 133A, 133B of the PD cycler 102 are also be equipped with or in communication with sensors (e.g., force sensors) for detecting forces acting on the actuators 133A, 133B as the cassette 112 is pressed against the cassette interface 110. If, for example, the actuators 133A, 133B are slightly rotated relative to the hexagonal recesses 175A, 175B in the plungers 161A, 161B of the cassette 112, the hexagonal keys 134A, 134B of the actuators 133A, 133B will not slide smoothly into the recesses 175A, 175B. As a result, a greater than desired force will be detected by the sensors. In response, a control unit to which both the sensors and the actuators 133A, 133B are connected will slowly cause the actuators to rotate until the force detected by the sensors falls below a maximum value, indicating the keys 134A, 134B are rotationally aligned with the recesses 175A, 175B and can thus slide smoothly into the recesses 175A, 175B.

Figure 9C:
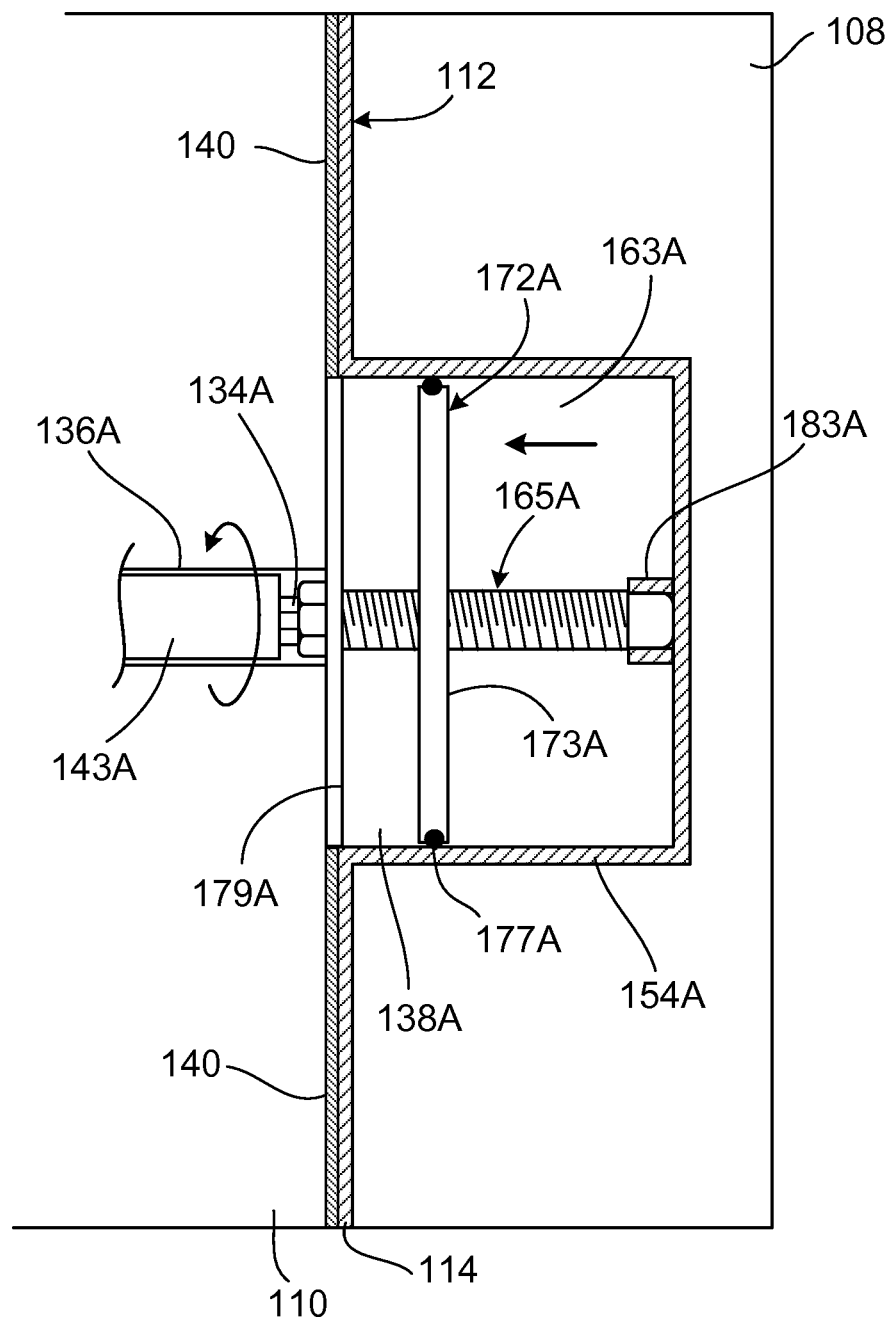

FIGS. 9A-9C illustrate the movement of the plunger 161A within the recessed region 163A of the base 156 to draw dialysis solution into the pump chamber 138A and to force dialysis solution out of the pump chamber 138A. It should be understood that the other plunger 161B would operate in a similar manner to pump dialysis solution to and from the other pump chamber 138B.

Referring to FIG. 9A, with the cassette 112 positioned adjacent to the cassette interface 110, the door 108 is closed over the cassette 112 such that the cassette 112 is contained within the cassette compartment 114 between the door 108 and the cassette interface 110. With the cassette 112 positioned in the cassette compartment 114, the inflatable pad within the door 108 is inflated to compress the cassette 112 between the door 108 and the cassette interface 110. This compression of the cassette 112 holds the projections 154A, 154B of the cassette 112 in the recesses 152A, 152B of the door 108 and presses the membrane 140 tightly against the raised ridges 167 extending from the planar surface of the rigid base 156 to form the enclosed fluid pathways 158 and dome regions 146 (shown in FIG. 6).

During operation, with the cassette 112 secured within the cassette compartment 114, the actuators 133A, 133B are rotated to axially reciprocate the plungers 161A, 161B within the recessed regions 163A, 163B of the base 156 of the cassette 112. Typically, as the actuator 133A is rotated in a direction to move the plunger 161A away from the cassette interface 110, as shown in FIG. 9A, the other actuator 133B is rotated in the opposite direction to move the plunger 161B toward the cassette interface 110, and vice versa. As a result, dialysis solution is drawn into the pump chamber 138A at the same time that dialysis solution is expelled from the pump chamber 138B, and vice versa.

As shown in FIG. 9B, the screw 165A of the plunger 161A is rotated until the plunger head assembly 172A has moved fully into the recessed region 163A formed by the hollow protrusion 154A of the base 156. This movement increases the volume of the pump chamber 138A formed between the plunger head assembly 172A and the oval cap 179A, and thus causes dialysis solution to be drawn into the pump chamber 138A from the fluid pathways 158 of the cassette via the inlet port 185A (shown in FIG. 4). Because the cross-sectional area is substantially constant along the depth of the recessed region 163A, the linear distance travelled by the plunger head assembly 172A can be used to easily determine the volume of dialysis solution drawn into the fluid pump chamber 138A. In particular, the volume of fluid drawn into the fluid pump chamber 138A is the linear distance travelled by the plunger head assembly 172A multiplied by the cross-sectional area of the recessed region 163A. In addition, the linear distance travelled by the plunger head assembly 172A can be determined based on the number of revolutions of the screw 165A, which is equal to the number of revolutions of the actuator 133A used to rotate the screw 165A. Thus, the volume of solution drawn into the fluid pump chamber 138A can be determined based on the number of revolutions made by the actuator 133A.

After drawing the dialysis solution into the pump chamber 138A, the dialysis solution is forced out of the pump chamber 138A by rotating the screw 165A in the opposite direction, causing the plunger head assembly 172A to move back toward the cassette interface 110 of the PD cycler 102, as shown in FIG. 9C. The screw 165A is typically rotated by the actuator 133A until the plunger head assembly 172A reaches the outlet port 187A (shown in FIGS. 4 and 5) so that substantially all of the dialysis solution is forced out of the fluid pump chamber 138A via the outlet port 187A.

This process of drawing dialysis solution into the fluid pump chamber 138A and then forcing the dialysis solution out of the fluid pump chamber 138A is repeated until a desired volume of dialysis solution has been pumped to or from a location (e.g., to or from the patient).

As noted above, while forcing dialysis solution into and out of the pump chambers 138A, 138B, certain inflatable members 142 of the PD cycler 102 can be selectively inflated to direct the pumped dialysis solution along desired pathways in the cassette 112.

Referring back to FIGS. 1 and 2, during PD treatment, the patient line 130 is connected to a patient's abdomen via a catheter, and the drain line 132 is connected to a drain or drain receptacle. The PD treatment typically begins by emptying the patient of spent dialysis solution that remains in the patient's abdomen from the previous treatment. To do this, the pump of the PD cycler 102 is activated to cause the actuators 133A, 133B to rotate and selected inflatable members 142 are inflated to cause the spent dialysis solution to be drawn into the fluid pump chambers 138A, 138B of the cassette 112 from the patient. The spent dialysis solution is then pumped from the fluid pump chambers 138A, 138B to the drain via the drain line 132.

After draining the spent dialysis solution from the patient, heated dialysis solution is transferred from the heater bag 124 to the patient. To do this, the pump of the PD cycler 102 is activated to cause the actuators 133A, 133B to rotate and certain inflatable members 142 of the PD cycler 102 are inflated to cause the warmed dialysis solution to be drawn into the fluid pump chambers 138A, 138B of the cassette 112 from the heater bag 124 via the heater bag line 128. The warmed dialysis solution is then pumped from the fluid pump chambers 138A, 138B to the patient via the patient line 130.

Once the dialysis solution has been pumped from the heater bag 124 to the patient, the dialysis solution is allowed to dwell within the patient for a period of time. During this dwell period, toxins cross the peritoneum into the dialysis solution from the patient's blood. As the dialysis solution dwells within the patient, the PD cycler 102 prepares fresh dialysate for delivery to the patient in a subsequent cycle. In particular, the PD cycler 102 pumps fresh dialysis solution from one of the four full dialysis solution bags 122 into the heater bag 124 for heating. To do this, the pump of the PD cycler 102 is activated to cause the actuators 133A, 133B to rotate and certain inflatable members 142 of the PD cycler 102 are inflated to cause the dialysis solution to be drawn into the fluid pump chambers 138A, 138B of the cassette 112 from the selected dialysis solution bag 122 via its associated line 126. The dialysis solution is then pumped from the fluid pump chambers 138A, 138B to the heater bag 124 via the heater bag line 128.

After the dialysis solution has dwelled within the patient for the desired period of time, the spent dialysis solution is pumped from the patient to the drain. The heated dialysis solution is then pumped from the heater bag 124 to the patient where it dwells for a desired period of time. These steps are repeated with the dialysis solution from two of the three remaining dialysis solution bags 122. The dialysis solution from the last dialysis solution bag 122 is typically delivered to the patient and left in the patient until the subsequent PD treatment.

While the dialysis solution has been described as being pumped into the heater bag 124 from a single dialysis solution bag 122, dialysis solution can alternatively be pumped into the heater bag 124 from multiple dialysis solution bags 122. Such a technique may be advantageous, for example, where the dialysis solutions in the bags 122 have different concentrations (e.g., different dextrose concentrations) and a desired concentration for treatment is intermediate to the concentrations of the dialysis solution in two or more of the bags 122.

After completion of the PD treatment, the door 108 of the PD cycler is opened and the cassette 112 is removed from the cassette compartment 114 and discarded.

Because the PD system 100 does not require a vacuum system to draw liquid into the fluid pump chambers 138A, 138B, a substantially airtight seal between the door 108 and the cassette interface 110 is typically not required. Thus, as compared to systems including a vacuum system adapted to retract portions of the cassette membrane overlying pump chambers, the door sealing mechanism of the PD cycler 102 can be simpler and more cost effective. In addition, the reduced use of vacuum pressure relative to certain conventional cyclers can result in quieter operation.

While certain implementations have been described, other implementations are possible.

While the membrane 140 of the cassette 112 has been shown as being substantially flush with the top edges of the portions of the base 156 that form the recessed regions 163A, 163B, in certain implementations, the portions of the base 156 forming the recessed regions 163A, 163B extend beyond the membrane 140. In this way, the volumetric capacity of the fluid pump chambers 138A, 138B can be increased. In such implementation, the cassette interface of the PD cycler is provided with recesses to receive those portions of the base that form the recessed regions 163A, 163B and extend beyond the plane in which the membrane 140 lies. As a result of this arrangement, the membrane 140 still contacts the cassette interface such that the various inflatable valve members and sensors on the cassette interface are operable with the cassette.

While the recessed regions 163A, 163B of the base of the cassette 112 and the plunger head assemblies 172A, 172B have been described as being oval-shaped, any of various other shapes that substantially prevent rotation of the plunger head assemblies 172A, 172B within the recessed regions 163A, 163B while permitting translation movement of the plunger head assemblies 172A, 172B within the recessed regions 163A, 163B can be used. For example, these components can alternatively be polygonal (e.g., triangular, rectangular, hexagonal, etc.).

While the enlarged head 171A, 171B and the threaded shaft 169A, 169B of the screw 165A, 165B of the plunger 161A, 161B have been described as separate components that are attached to one another, the screw 165A, 165B can alternatively be formed (e.g., cast or molded) as a unitary structure.

Figure 10:
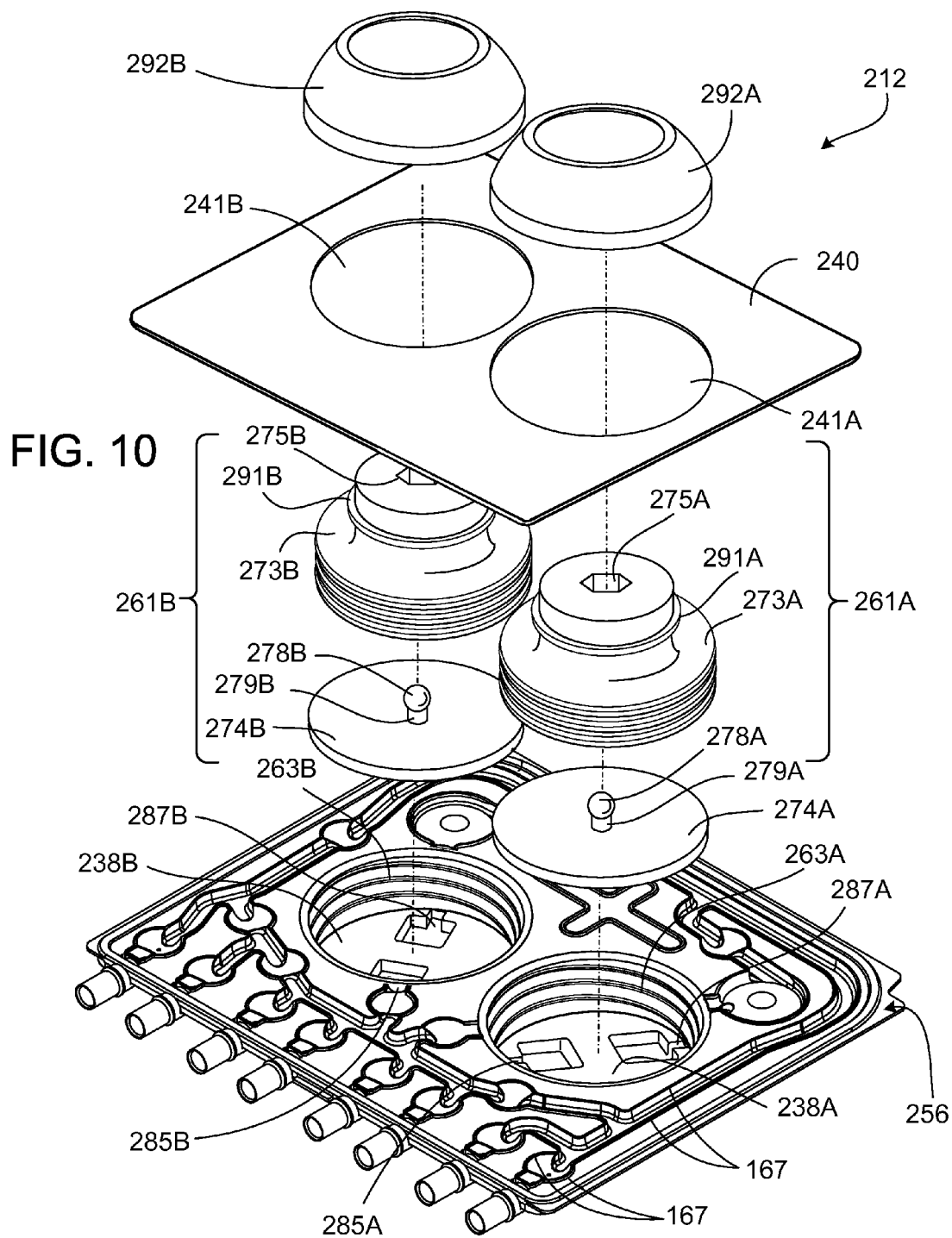
FIG. 10 is an exploded, perspective view of another PD cassette that includes a plunger that is rotatably and slidably disposed within a chamber of the cassette.

While the plungers 161A, 161B have been described as including rotatable shafts 165A, 165B that threadedly engage the oval disks 173A, 173B of the plunger head assemblies 172A, 172B to translate the plunger head assemblies 172A, 172B within the recessed regions 163A, 163B of the hollow portions 154A, 154B of the cassette base 156, other arrangements can be used to achieve axial translation of plunger head assemblies within recessed regions of the cassette base. FIG. 10, for example, illustrates an exploded view of a cassette 212 that includes plungers 261A, 261B that are rotatably disposed in cylindrical recessed regions 263A, 263B of a base 256 of the cassette 212. A membrane 240 is attached to the base 256 in the same way that the membrane 140 of the cassette 112 was described as being attached to the base 156 such that circular openings 241A, 241B in the membrane 240 align with the cylindrical recessed regions 263A, 263B of the base 256 and expose the plungers 261A, 261B disposed within those recessed regions. The plungers 261A, 261B threadedly engage the base 256 in a manner such that rotation of the plungers 261A, 261B by the actuators 133A, 133B is converted into translational motion of the plungers 261A, 261B. The translational motion of the plungers 261A, 261B can be used to draw liquid into and force liquid out of fluid pump chambers 238A, 238B formed between the plungers 261A, 162B and the bottom surfaces (from the perspective shown in FIG. 10) of the recessed regions 263A, 263B of the base 256.

Figure 11:
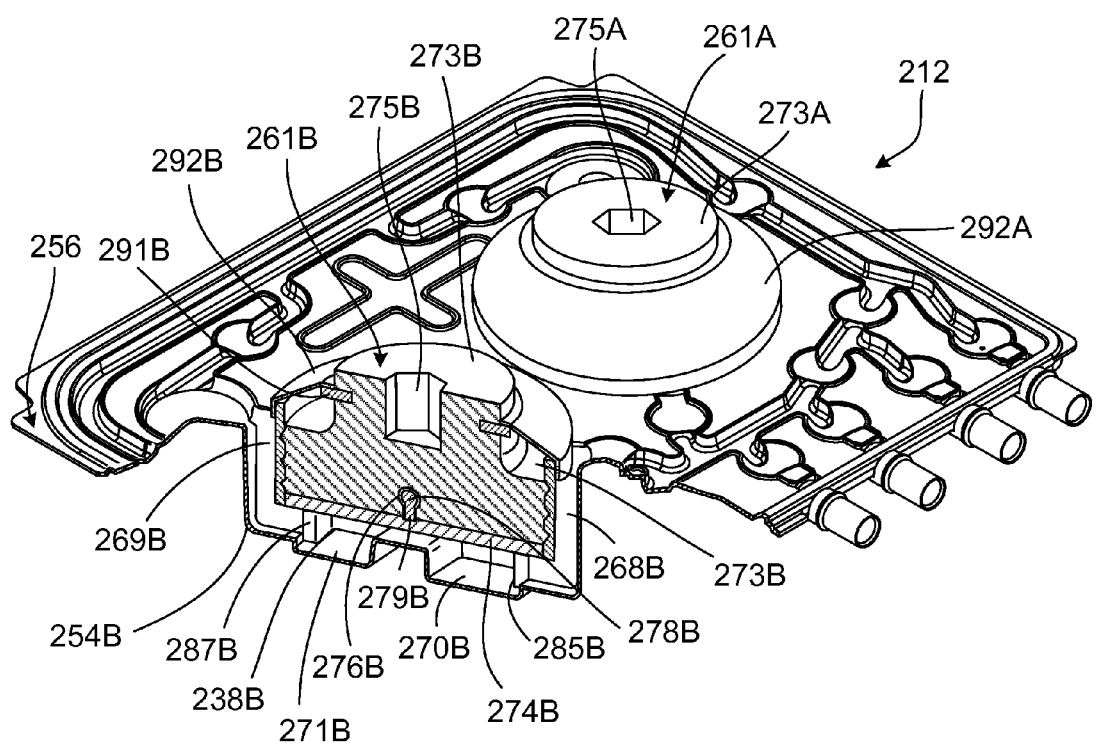
FIG. 11 is a perspective, cut-away view of the PD cassette of FIG. 10.
Figure 12:
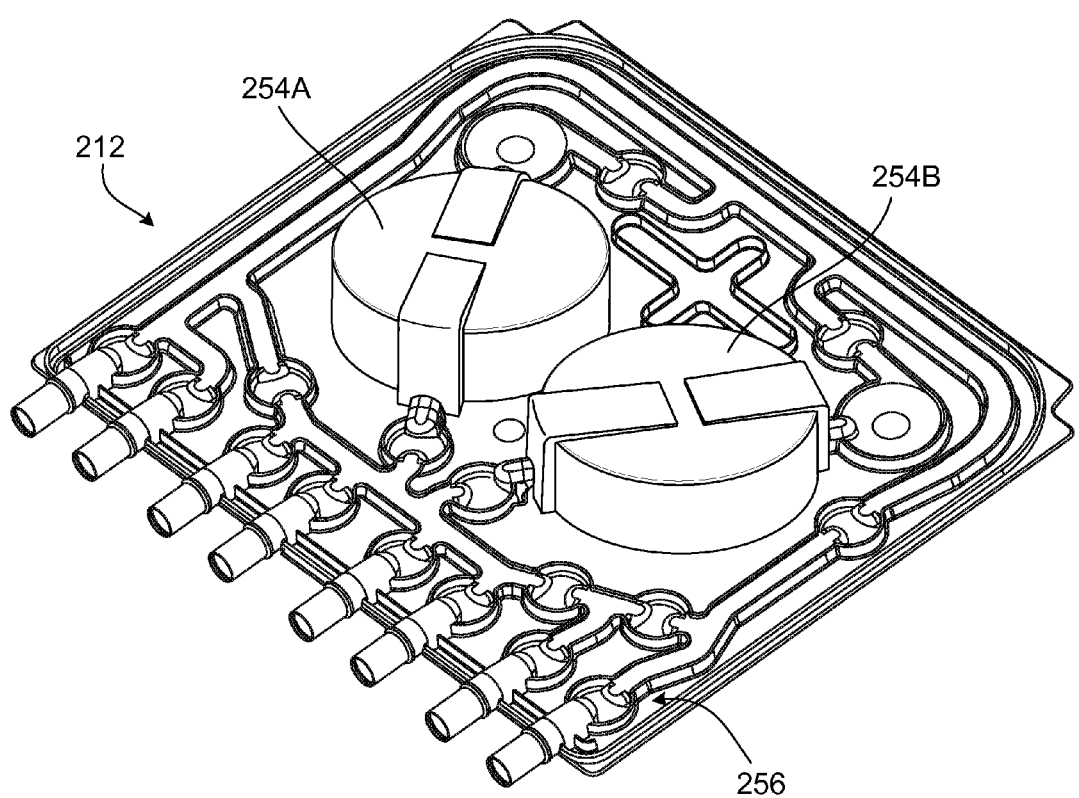
FIG. 12 is a perspective view of the PD cassette of FIG. 10, from a rigid base side of the PD cassette.

The base 256 of the cassette 212 is similar to the bases of those cassettes described above. However, the recessed regions 263A, 263B and fluid inlet and outlet passages leading to the recessed regions 263A, 263B have different configurations than the corresponding features in the cassette 112 described above. As shown in FIGS. 10-12, the base 256 includes hollow, substantially cylindrical projections 254A, 254B that form the cylindrical recessed regions 263A, 263B. Unlike the cassette base 156 described above, which includes fluid inlet and outlet ports near the ends of the recessed regions closest to the membrane 140, fluid inlet ports 285A, 285B and outlet ports 287A, 287B are formed in the side wall of the cylindrical projections 254A, 254B, near the ends of the recessed regions 263A, 263B opposite the membrane 140 (i.e., near the bottom ends (from the perspective shown in FIGS. 10 and 11) of the recessed regions 263A, 263B). Thus, when the cassette 212 is fully assembled, as shown in FIG. 11, the fluid inlet ports 285A, 285B and outlet ports 287A, 287B are positioned below the plungers 261A, 261B.

The portion of the base 256 that forms the recessed region 263B will now be described with reference to FIG. 11. Although not shown in detail in FIG. 11, it should be understood that the portion of the base 256 forming the other recessed region 263A, which underlies the plunger 261A, has generally the same construction and function as the recessed region 263B. Referring to FIG. 11, the base 256 of the cassette 212 forms vertical fluid passages 268B, 269B that extend from fluid channels formed along the top surface (from the perspective shown in FIG. 11) of the base 256 to the fluid inlet and outlet ports 285B, 287B. These passages 268B, 269B extend along the peripheral surface of the cylindrical projection 254B in which the plunger 261B is disposed. The surface region of the base 256 that underlies the plunger 261B forms channels 270B, 271B that are aligned with the fluid inlet and outlet ports 265B, 267B to allow fluid to flow underneath the plunger 261B and into and out of the fluid pump chamber 238B formed between the plunger 261B and the base 256 when the plunger 261B is translated within the recessed region 263B.

The plunger 261B of the cassette 212 will now be described with reference to FIGS. 10 and 11. The other plunger 261A of the cassette 212 is of identical structure and function and thus will not be separately described in detail. As shown in FIGS. 10 and 11, the plunger 261B includes a plug 273B to which a disk-shaped seal 274B is secured. The end of the plug 273B opposite the seal 274B forms a hexagonal recess 275B sized to receive the hexagonal key 134B of the actuator 133B (shown in FIG. 3) of a PD cycler. Thus, the actuator 133B can be used to rotate the plug 273B when the cassette 212 is loaded into the cassette compartment of the PD cycler. The plug 273B includes threads along its outer side wall that matingly engage threads along the inner surface of the recessed region 263B of the base 256. The engagement of these threads causes the plug 273B to move axially downward toward a bottom interior surface the base 256 (form the perspective of FIGS. 10 and 11) when the plug 273B is rotated in a first direction and causes the plug 273B to move axially upward away from the bottom surface of the base 256 when the plug 273B is rotated in a second, opposite direction.

The bottom portion of the plug 273B (from the perspective shown in FIGS. 10 and 11) includes a ball-shaped socket 276B. A ball 278B positioned atop a pin 279B extending from the top surface of the seal 274B is disposed in the ball-shaped socket 276B. The ball-shaped socket 276B is slightly larger than the ball 278B and is positioned along the axis of rotation of the plug 273B. The resulting mating engagement between the ball 278B and the socket 276B allows the ball 278B to freely rotate within the socket 276B, which allows the plug 273B to rotate relative to the seal 274B. As described below, this arrangement allows the translational movement of the plug 273B to be transmitted to the seal 274B while limiting (e.g., minimizing) the rotational movement transmitted to the seal 274B.

The seal 274B is typically formed of a resilient material, such as fluoroelastomer (e.g., Viton® fluoroelastomer), polytetrafluoroethylene (PTFE), or rubber. The seal 274B typically has a diameter that is slightly larger than the diameter of the recessed region 263B of the base 256 such that the seal 274B forms a liquid-tight seal with the base 256. In certain implementations, the diameter of the seal 274B is about 1.5 millimeters to about 6.5 millimeters greater than the inner diameter of the hollow projection 254B, which forms the recessed region 263B.

Figure 13C:
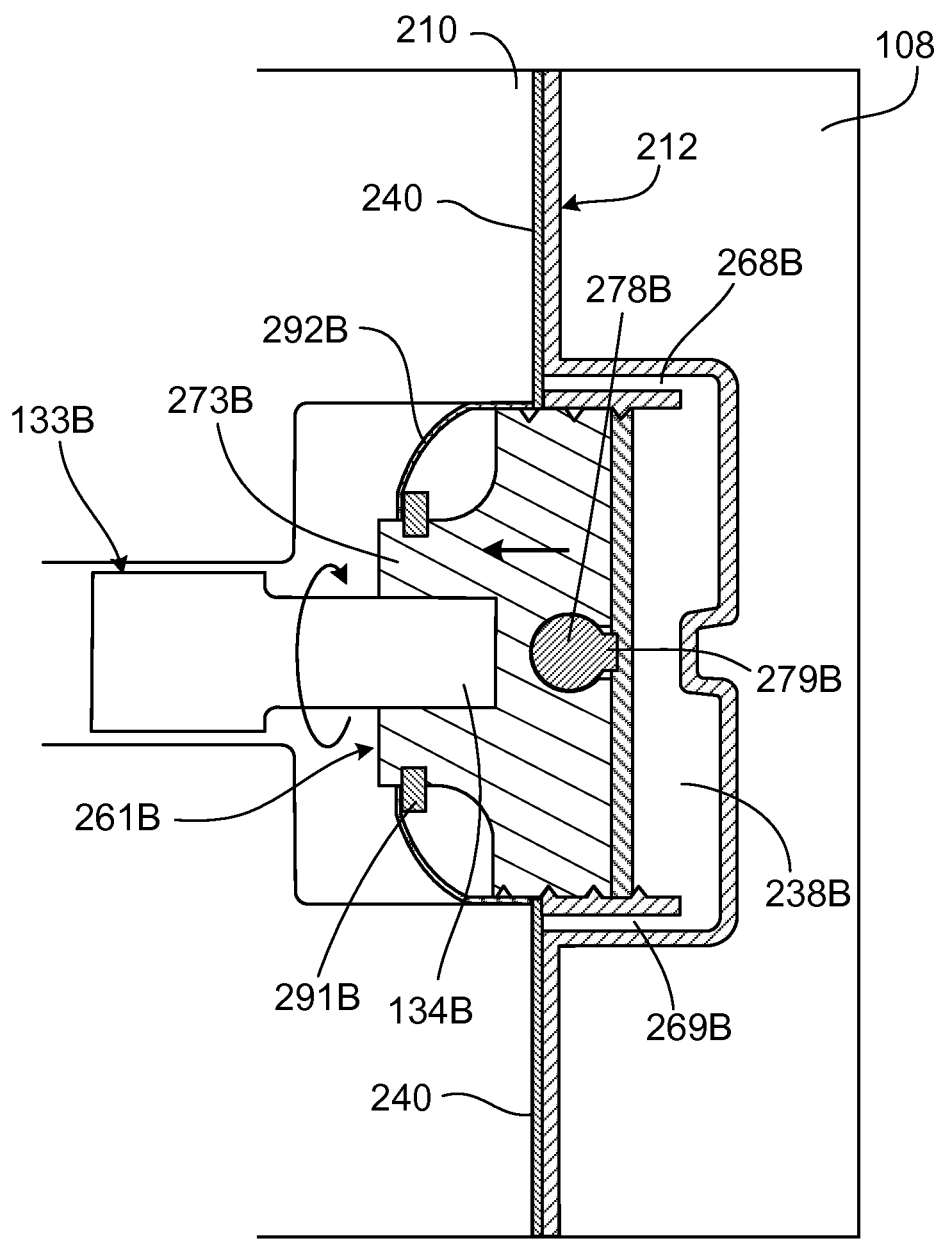

Still referring to FIGS. 10 and 11, the top region of the plug 273B also includes an annular channel that retains a ring 291B. A flexible dust cover 292B is attached in one end region to the ring 291B and in an opposite end region to a portion of the cassette base 256 surrounding the recessed region 263B. The annular channel in which the ring 291B is retained is slightly larger than the ring 291B such that the plug 273B can rotate relative to the ring 291B during use. As a result of this arrangement, the ring 291B and the dust cover 292B are substantially rotationally fixed relative to the base 256. Thus, as the plug 273B is rotated during use, causing it to translate within the recessed region 263B of the base 256, the ring 291B and the dust cover 291B remain rotationally fixed. In FIG. 11, the plug 273B is shown in a partially retracted state such that the dust cover 292B is pulled relatively taut. Due to the flexibility of the dust cover 292B, as the plug 273B is advanced into the recessed region 263B of the base 256, the dust cover 292B folds over slightly upon itself without significantly impacting or resisting the movement of the plug 273B. Due to substantially continuous seals (e.g., thermal or adhesive seals) formed between the dust cover 292B and the ring 291B and between the dust cover 292B and the base 256, dust and other contaminants can be prevented from contacting the threaded region of the plug 273B during use. This can reduce the likelihood of dust and other contaminants reaching the fluid pump chamber 238B FIGS. 13A-13C show the cassette 212 disposed within the cassette compartment of a PD cycler during different stages of the pumping process. The PD cycler illustrated in FIGS. 13A-13C is generally the same as the PD cycler 102 described above. However, a cassette interface 210 of the illustrated PD cycler includes larger recesses 206A, 206B surrounding the actuators 133A, 133B in order to accommodate the plungers 261A, 261B as they are retracted into the cassette interface 210. In FIG. 13A, the plunger 261B is in a substantially fully retracted state such that the plunger 261B is positioned in the end of the recessed region 263B nearest the cassette interface 110 of the PD cycler 102. In this position, the fluid pump chamber 238B is at its maximum operating volume and contains dialysis solution. The cassette 212 is compressed between the inner surfaces of the door 108 and the cassette interface 210 in the same way as described above with respect to cassette 112 such that the membrane 240 is compressed against the base 256 to form a series of fluid passageways that fluidly connect the fluid pump chambers 238A, 238B to various tubing connectors 260 of the cassette 212.

With dialysis solution contained in the fluid pump chamber 238B of the cassette 212, the actuator 133B of the PD cycler is rotated to drive the plunger 261B toward the end of the recessed region 263B opposite the cassette interface 110. The plunger 261B is advanced in this way until it contacts the end surface of the recessed region 263B of the base 256, as shown in FIG. 13B. As the plunger is advanced, the dialysis solution flows through the channel 271B, out the fluid outlet port 287B, and into the passage 269B. Because the plug 273B is allowed to rotate relative to the seal 274B as the plunger 261B is advanced, rotation of the seal 274B within the recessed region 263B is limited (e.g., minimized). As a result, the amount of friction experienced between the seal 274B and the inner surface of the hollow protrusion 254B is limited (e.g., minimized). This can reduce wear and tear on the seal 274B, which can prolong the life of the seal 274B and reduce the risk of leaks.

In FIG. 13C, the actuator 133B is being rotated in the opposite direction such that the plunger 261B is retracted toward the cassette interface 110 of the PD cycler 102. As a result of this movement, dialysis solution is drawn into the fluid pump chamber 238B. In particular, as the plunger 261B retracts, fluid passes through the passage 268B, fluid inlet port 285B, and channel 270B into the fluid pump chamber 238B. Because the channels 270B, 271B are recessed relative to the end surface 277B, the channels 270B, 271B ensure fluid communication between the fluid pump chamber 238B and the inlet and outlet ports 285B, 287B even when the plunger 261B has been fully advanced into contact or near contact with the end surface 277B of the recessed region 263B of the base 256.

While the seal 274B has been described as being secured to the plug 273B via a ball and socket joint, any of various other types of connections that allow the plug to rotate relative to the seal can be used.

In addition, while the cassette 212 includes the dust cover 292B, which can help to prevent contaminants from contacting the threads of the plug 273B and making their way into the fluid pump chamber 238B, in certain implementations, the cassette includes no such dust cover.

Figure 14:
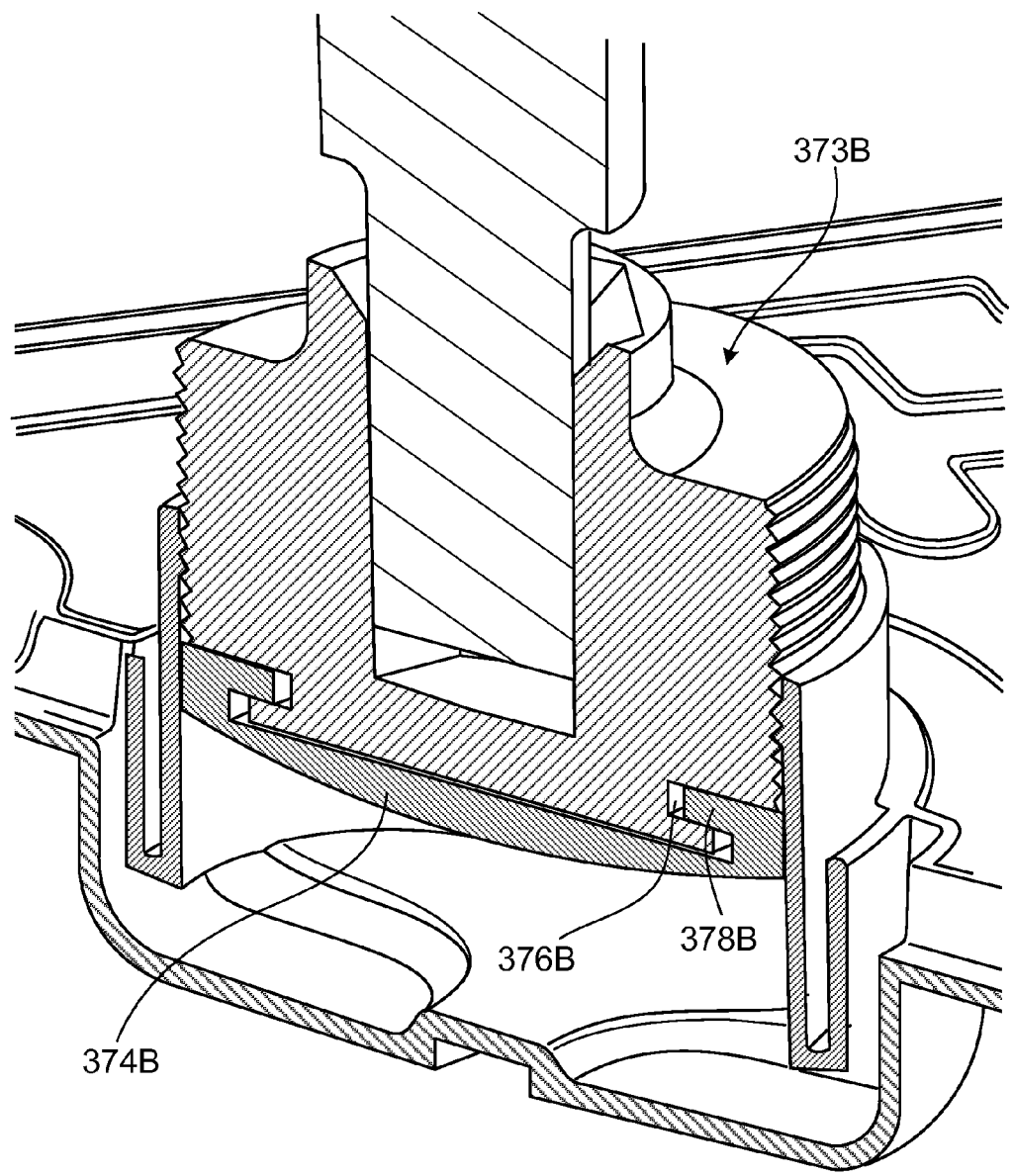
FIG. 14 is a perspective cut-away view of another PD cassette that includes a plunger that is rotatably and slidably disposed within a chamber of the cassette.

As shown in FIG. 14, a plunger plug 373B, which includes no dust cover attached thereto, defines an annular recess 376B into which an undercut 378B of a seal 374B is received. The annular recess 376B is slightly larger than the undercut 378B such that the plug 373B can rotate relative to the seal 374B. In certain implementations, the interface between the recess 376B and the undercut 378B is lubricated to reduce friction between those components and thus allow those components to rotate more freely relative to one another. Apart from those differences noted above, the cassette illustrated in FIG. 14 is generally the same as the cassette 212 described above.

While the cassette interface 110 of the PD cycler 102 has been described as including locating pins 148 that help to ensure that the hexagonal recesses in the plungers of the cassette are aligned with the hexagonal keys 134A, 134B of the actuators 133A, 133B when the cassette is positioned in the cassette compartment 114, other structures or techniques can be used to ensure this alignment. In certain implementations, for example, the cassette is held in place only the by the mating engagement between the hexagonal keys 134A, 134B and the hexagonal recesses 175A, 175B of the plungers 161A, 161B or the hexagonal recesses 275A, 275B of the plungers 261A, 261B. In some implementations, the cassette is placed against the door of the PD cycler with the hollow projections of the cassette disposed in recesses of the PD cycler's door, and the cassette is held in this position by retainer clips attached to the door. Upon closing the door, the actuators of the PD cycler align with the plungers of the cassette.

While the actuators 133A, 133B of the PD cyclers above have been described as including hexagonal keys 134A, 134B that matingly engage hexagonal recesses formed in the plungers, keys and recesses having any of various other mating shapes that permit rotational forces to be transmitted from the actuators to the plungers can alternatively be used. For example, triangular, square, pentagonal, octagonal, star-shaped, or oval-shaped keys and recesses can be used.

While the door 108 of each of the PD cyclers above has been described as including an inflatable pad that, when inflated, can press the cassette against the cassette interface, the inflatable pad can alternatively be positioned behind the cassette interface such that the cassette interface can be moved toward the door 108 to compress the cassette therebetween. Similarly, as an alternative to an inflatable pad, any of various mechanisms that can be operated to move a surface of the door 108 toward the cassette interface or vice versa can be used.

While the door 108 of the PD cyclers described above are shown as being positioned on a front face of the PD cyclers, the doors can alternatively be positioned at various other locations on the PD cyclers. For example, the doors could be positioned on a top face of the PD cycler such that the cassette is slid into the cassette compartment in a substantially horizontal orientation instead of a substantially vertical orientation. In some implementations, the door and the cassette interface of the PD cycler are positioned at an angle of about 10 to about 35 degrees to vertical when the PD cycler is rested on a horizontal surface. It has been found that this configuration makes it easier for the user to load the cassette into the cassette compartment.

While the cassettes discussed above have two pump chambers, the cassettes can alternatively have more or fewer than two pump chambers.

While each of the pump chambers of the cassettes described above has been described as including a fluid inlet port and a fluid outlet port, in certain implementations, the pump chambers include a single port that is used as both an inlet and an outlet.

While operation of the cassettes described above involves applying rotational force to the plungers in order to cause translational motion of the plungers within the recessed regions of the cassette base, certain systems are designed to cause translational motion of plungers by applying a linear force to the plungers. In certain implementations, for example, the actuator is a linearly drivable member that is coupled to a plunger head disposed in a recess of the cassette in a manner to allow the actuator to translate the plunger head back and forth within the recess of the cassette. In such implementations, the actuator and the plunger head can be mechanically coupled, magnetically coupled, and/or adhesively coupled to one another.

Figure 15:
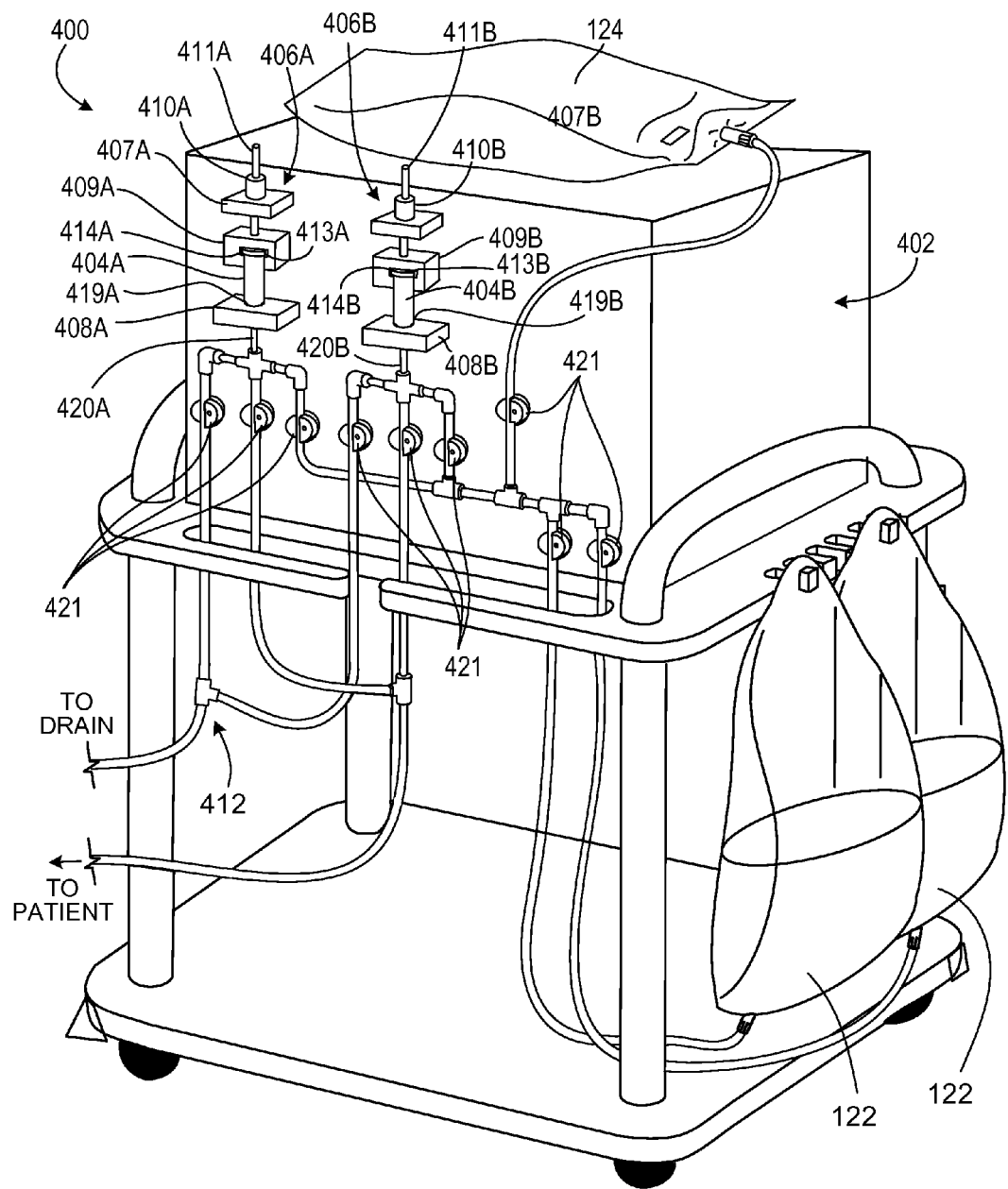
FIG. 15 is a perspective view of a PD system that includes a PD machine and a PD solution delivery set connected to the PD machine in a manner such that syringes of the PD solution delivery set can be operated by drive mechanisms of the PD machine.

In addition, while each of the systems described above include a PD cycler that cooperates with a PD cassette to pump fluid to and from a patient, non-cassette based devices can alternatively be used to pump fluid to and from the patient. As shown in FIG. 15, for example, a PD system 400 includes a PD solution delivery set 412 that is connected to a PD machine 402. The PD solution delivery set 412 includes two syringes 404A, 404B and a series of interconnected fluid lines (i.e., tubes) that are connected to the syringes 404A, 404B for drawing PD solution into the syringes 404A, 404B from multiple different sources (e.g., the dialysate bags 122, the heater bag 124, and a peritoneal cavity of a patient) and for delivering PD solution from the syringes 404A, 404B to multiple different destinations (e.g., the heater bag 124, the peritoneal cavity of the patient, and a drain). The PD machine 402 includes drive mechanisms 406A, 406B that engage the syringes 404A, 404B, respectively, and can be operated in a manner to cause fluid to be drawn into the syringes and to cause fluid to be expelled from the syringes.

Each of the drive mechanisms 406A, 406B includes a stationary top member 407A, 407B, a stationary bottom member 408A, 408B, and an intermediate member 409A, 409B that can be moved between the top and bottom members. The top member 407A, 407B, which is rigidly fixed to the PD machine 402, includes a motor 410A, 410B that is operatively engaged with a threaded shaft 411A, 411B in a manner to axially displace the threaded shaft 411A, 411B upwardly or downwardly, depending on the direction of rotation of the motor 410A, 410B. The threaded shaft 411A, 411B is connected to the intermediate member 409A, 409B in a manner such that the axial motion of the threaded shaft 411A, 411B is transmitted to the intermediate member 409A, 409B, but the rotational motion of the threaded shaft 411A, 411B is not transmitted to the intermediate member 409A, 409B. In certain implementations, for example, the lower end of the threaded shaft 411A, 411B includes a ball member that mates with a socket formed in the intermediate member 409A, 409B to allow translational forces but not rotational forces to be transmitted from the threaded shaft 411A, 411B to the intermediate member 409A, 409B. However, any of various other mechanisms capable of achieving this type of motion can alternatively be used.

The intermediate member 409A, 409B includes a slot 413A, 413B sized and shaped to receive a flange 414A, 414B that extends from an outer plunger shaft 415A, 415B of a plunger assembly 417A, 417B (shown in FIG. 16) of the syringe 404A, 404B. The intermediate member 409A, 409B also includes a recess 418A, 418B sized and shaped to receive a portion of the outer plunger shaft 415A, 415B located below the flange 414A, 414B. In this way, the plunger assembly 417A, 417B of the syringe 404A, 404B can be fixed to the intermediate member 409A, 409B of the drive mechanism such that the plunger assembly 417A, 417B moves axially along with the intermediate member 409A, 409B when the drive mechanism 406A, 406B is in operation. The bottom member 408A, 408B, which is rigidly fixed to the PD machine 402, includes a recess 419A, 419B that is sized and shaped to releasably engage an end region of a fluid containment cylinder 420A, 420B of the syringe 404A, 404B to substantially prevent the fluid containment cylinder 420A, 420B from moving axially (i.e., translating) relative to the PD machine 402 as the drive mechanism 406A, 406B reciprocates the plunger assembly 417A, 417B of the syringe 404A, 404B.

The PD cycler 402 also include multiple valves 421 that engage the fluid lines of the PD solution delivery set 412 at selected locations along those lines. The valves 421 are typically pinch valves that can be used to pinch and occlude a portion of a fluid line threaded through the valve. However, any of various other types of valves that can effectively prevent flow through the fluid lines can alternatively or additionally be used. The valves 421 can be operated in conjunction with the drive mechanisms 406A, 406B to control fluid flow through the PD solution delivery set 412. The valves 421 and the drive mechanisms 406A, 406B can, for example, be connected to a common control unit (e.g., processor) that is used to control the operation of those devices. Typically, the drive mechanisms 406A, 406B are operated in a manner so that fluid is drawn into one of the syringes 404A, 404B as fluid is expelled from the other syringe 404A, 404B. However, other techniques can be used.

Figure 16:
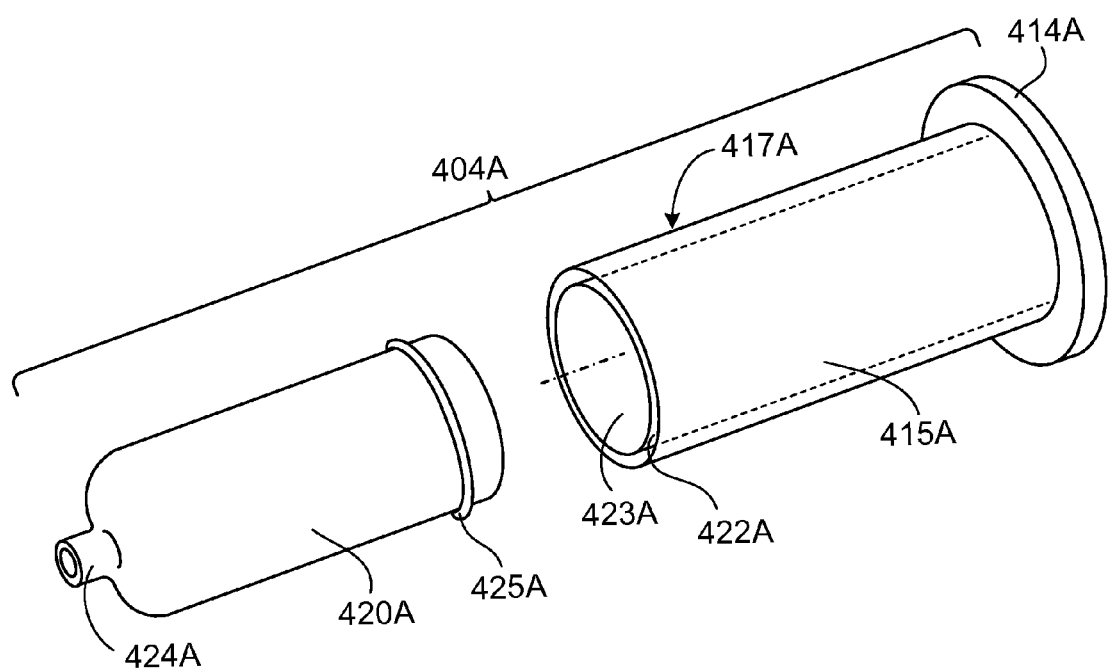
FIG. 16 is a perspective, exploded view of one of the syringes of the PD solution set illustrated in FIG. 15.

FIG. 16 shows a perspective, exploded view of the syringe 404A of the PD solution delivery set 412. The syringe 404B is identical in structure and function to the syringe 404A. Therefore, only the syringe 404A will be described in detail. The plunger assembly 417A of the syringe 404A includes the outer plunger shaft 415A and an inner plunger shaft 422A concentrically arranged within the hollow outer plunger shaft 415A. Both the outer plunger shaft 415A and the inner plunger shaft 422A are attached to and extend from the flange 414A. The outer plunger shaft 415A is sized and shaped to surround the fluid containment cylinder 420A, while the inner plunger shaft 422A is sized and shaped to be disposed within the fluid containment cylinder 420A. A resilient seal 423A is connected to the free end of the inner plunger shaft 422A and is also sized and shaped to fit within the fluid containment cylinder 420A. The seal 423 A has a slightly larger diameter than the inner diameter of the fluid containment cylinder 420A. The outer diameter of the seal 423A can, for example, be about 0.01 inch to about 0.03 inch (e.g., about 0.02 inch) larger than the inner diameter of the fluid containment cylinder 420A. Due to the size, shape, and resiliency of the seal 423A, a liquid-tight seal is formed between the seal 423A and the inner surface of the fluid containment cylinder 420 when the inner plunger shaft 422A is disposed within the fluid containment cylinder 420.

Still referring to FIG. 16, the fluid containment cylinder 420A includes a nozzle 424A that is attached (e.g., thermally or adhesively bonded) to a fluid line of the PD solution delivery set 412 (shown in FIG. 15). An o-ring 425A is secured around an outer surface of the fluid containment cylinder 420A, near an opposite end of the fluid containment cylinder 420A. The o-ring 425A is formed of a resilient material and the outer diameter of the o-ring is slightly greater than the inner diameter of the outer plunger shaft 415A such that a liquid-tight seal is created between the o-ring 425A and the inner surface of the outer plunger shaft 415A.

The outer plunger shaft 415A covers the inner plunger shaft 422A so that in the event that fluid passes through the seal 423A and comes into contact with inner plunger shaft 422A, the person handling the syringe 404A will not come into contact with the fluid. In addition, the o-ring 425A secured to the fluid containment cylinder 420 helps to ensure that any fluid that leaks into the space between the inner plunger shaft 422A and the outer plunger shaft 415A remains contained within that space. This construction of the syringe 404A likewise ensures that contaminants from the environment of from the hands of the user will not come into contact with the fluid within the fluid containment cylinder 420.

FIGS. 17A-17D diagrammatically illustrate operation of the syringe 404A to draw PD solution into the fluid containment cylinder 420A of the syringe 404A and to expel PD solution from the fluid containment cylinder 420A of the syringe 404A during PD treatment. It should be understood that the other syringe 404B would operate in a similar manner to pump dialysis solution to and from the fluid containment cylinder 420B of the other syringe 404B.

Referring to FIG. 17A, in an initial state, the plunger shaft assembly 417A is fully advanced such that the seal 423A at the end of the inner plunger shaft 422A is in contact with or near contact with the end surface of the fluid containment cylinder 420A. In this state, a fluid pump chamber 438A formed between the seal 423A and the end surface of the fluid containment cylinder 420A contains substantially no liquid.

As shown in FIG. 17B, as the plunger shaft assembly 417A is moved upward by moving the intermediate member 409A of the drive mechanism 406A (shown in FIG. 15) to which the flange 414A of the plunger shaft assembly 417A is connected, PD solution is drawn into the pump chamber 438A. Typically, as the drive mechanism 406A is operated to draw PD solution into the pump chamber 438A of the syringe 404A, the other drive mechanism 404B is operated to expel PD solution from the syringe 404B, and vice versa.

The plunger shaft assembly 417A continues to be retracted until the plunger shaft assembly is in the fully retracted position and the fluid pump chamber 438A is full, as shown in FIG. 17C. Because the cross-sectional area is substantially constant along the length of the fluid containment cylinder 420A, the linear distance travelled by the plunger shaft assembly 417A can be used to easily determine the volume of PD solution drawn into the fluid pump chamber 438A. In particular, the volume of PD solution drawn into the fluid pump chamber 438A is the linear distance travelled by the seal 423A of the plunger shaft assembly 417A multiplied by the cross-sectional area of the fluid containment cylinder 420A. In addition, the linear distance travelled by the seal 423A can be determined based on the number of revolutions of the motor of the drive mechanism 404A. Thus, the volume of PD solution drawn into the fluid pump chamber 438A can be determined based on the number of revolutions made by the motor of the drive mechanism 406A.

After drawing the PD solution into the pump chamber 438A, the PD solution is forced out of the pump chamber 438A by simply operating the drive mechanism 406A in the opposite direction (e.g., by running the motor 410A in reverse) and causing the plunger shaft assembly 417A to be advanced relative to the stationary fluid containment cylinder 420A.

This process of drawing dialysis solution into the fluid pump chamber 438A and then forcing the dialysis solution out of the fluid pump chamber 438A is repeated until a desired volume of PD solution has been pumped to or from a location (e.g., to or from the patient). As noted above, while forcing dialysis solution into and out of the pump chambers 438A, 438B, the valves 421 of the PD machine 402 are selectively inflated to direct the pumped dialysis solution along desired pathways formed by the series of fluid lines of the PD solution delivery set 412.

Although not shown in FIG. 15, the PD cycler 402 can be equipped with a touch screen and related control buttons similar to those described above with respect to the PD cycler 100.

While the plunger assemblies 417A, 417B of the syringes 404A, 404B have been described as being mechanically attached to or gripped by the drive mechanisms 406A, 406B of the PD machine 402, other techniques can be used to secure the plunger assemblies to the drive mechanisms. In certain implementations, for example, a drivable member of the drive mechanism includes one or more magnets and the plunger is equipped with one or more magnetically attractive members (e.g., plates) such that the plunger can be magnetically coupled to the plunger. Alternatively or additionally, one or both contacting surfaces of the plunger and the drive member can be provided with adhesive such that the drive member can be adhesively coupled to the plunger.

While the o-ring 425A has been described as being secured to an outer surface of the fluid containment cylinder 420A, in certain implementations, an o-ring is alternatively or additionally secured to the inner surface of the outer plunger shaft 415A. Such an o-ring can, for example, be attached to the inner surface of the outer plunger shaft 415A near the end of the outer plunger shaft 415A opposite the flange 414A. This arrangement can further ensure that contaminants are prevented from entering or exiting the space between the inner and outer plunger shafts.

While the PD system 400 has been described as including two drive mechanisms and the PD solution delivery set 412 has been described as including two syringes that are operated by those drive mechanisms, the PD machine and PD solution delivery set can alternatively include only one drive mechanism and syringe, respectively, or the PD machine and PD solution delivery set can include three or more drive mechanisms and syringes, respectively.

While certain PD cyclers above have been described as including a touch screen and associated buttons, the PD cyclers can alternatively or additionally include other types of screens and user data entry systems. In certain implementations, for example, the cycler includes a display screen with buttons (e.g., feather touch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

While the cassettes and fluid delivery sets described above have been described as being part of a PD system, these types of cassettes and fluid delivery sets can be used in any of various other types of medical fluid pumping systems. Other examples of medical fluid pumping systems with which cassettes fluid delivery sets described herein can be used include hemodialysis systems, blood perfusion systems, and intravenous infusion systems.

Similarly, while the cassettes and fluid delivery sets have been described as being used to pump dialysis solution, other types of dialysis fluids can be pumped through the cassettes. As an example, in the case of cassettes or fluid delivery sets used with hemodialysis machines, blood can be pumped through the cassettes or fluid delivery sets. In addition, priming solutions, such as saline, can similarly be pumped through cassettes or fluid delivery sets using the various different systems and techniques described above. Similarly, as an alternative to dialysis fluids, any of various other types of medical fluids can be pumped through the above-described cassettes and fluid delivery sets depending on the type of medical fluid pumping machines with which the cassettes or fluid delivery sets are used.

What is claimed is:

1. A medical fluid pumping system, comprising:
a medical fluid pumping machine defining a cassette enclosure, the medical fluid pumping machine comprising an actuator; and
a medical fluid cassette configured to be disposed within the cassette enclosure of the medical fluid pumping machine, the medical fluid cassette comprising
a base defining a recess; and
a plunger slidably disposed within the recess of the base, the plunger comprising a rotatable member and a seal connected to the rotatable member in a manner such that rotation of the rotatable member causes axial movement of the rotatable member and the seal relative to the base, the seal being configured to cooperate with the base such that a substantially liquid-tight seal is maintained between the plunger and the base as the plunger slides axially within the recess, the rotatable member, the seal, and the base cooperating to at least partially define a fluid pump chamber,
wherein, when the medical fluid cassette is disposed within the cassette enclosure of the medical fluid pumping machine, the actuator can be operated to axially displace the plunger within the recessed region of the base to force fluid out of the fluid pump chamber and to draw fluid into the fluid pump chamber.

2. The medical fluid pumping system of claim 1, wherein axially displacing the plunger in a first direction forces fluid out of the fluid pump chamber and axially displacing the plunger in a second direction draws fluid into the fluid pump chamber.

3. The medical fluid pumping system of claim 1, wherein the rotatable member comprises a plunger head having threads that matingly engage threads of the base to cause axial movement of the plunger head and the seal when the plunger head is rotated.

4. The medical fluid pumping system of claim 3, further comprising a member that is connected to the plunger head in a manner such that the plunger head can rotate relative to the member, and a flexible cover connected at one end to the base of the cassette and connected at an opposite end to the member.

5. The medical fluid pumping system of claim 1, wherein the medical fluid cassette comprises a membrane attached to the base.

6. The medical fluid pumping system of claim 5, wherein the membrane forms an opening that overlies the recess of the base.

7. The medical fluid pumping system of claim 6, wherein the membrane is attached to an annular portion of the base surrounding the recess.

8. The medical fluid pumping system of claim 1, wherein the actuator comprises a rotatable member, and the plunger defines a recess configured to matingly engage the rotatable member.

9. The medical fluid pumping system of claim 1, wherein the the seal forms the substantially liquid tight seal with the base.

10. The medical fluid pumping system of claim 1, wherein the medical fluid pumping machine is a dialysis machine.

11. The medical fluid pumping system of claim 1, wherein the base comprises a first end region and a second end region, the first end region being located farther from the actuator than the second end region when the medical fluid cassette is disposed within the cassette enclosure of the medical fluid pumping machine, and the first end region defining a fluid inlet port and a fluid outlet port.

12. The medical fluid pumping system of claim 1, wherein the seal is disk-shaped.

13. The medical fluid pumping system of claim 1, wherein the seal comprises a ball that matingly engages a socket defined in the rotatable member to allow the rotatable member to rotate relative to the seal.

14. The medical fluid pumping system of claim 1, wherein the rotatable member comprises a plug defining an annular channel and a ring disposed in the annular channel and configured to rotate relative to the plug.

15. A medical fluid cassette, comprising:
a base defining a recess;
a membrane attached to the base to form fluid passageways between the membrane and the base; and
a plunger slidably disposed within the recess of the base, the plunger comprising a rotatable member and a seal connected to the rotatable member in a manner such that rotation of the rotatable member causes axial movement of the rotatable member and the seal relative to the base, the seal being configured to cooperate with the base such that a substantially liquid-tight seal is maintained between the plunger and the base as the plunger slides axially within the recess, the rotatable member, the seal, and the base cooperating to at least partially define a fluid pump chamber,
wherein, when the plunger is displaced in a first direction, fluid is forced out of the fluid pump chamber, and when the plunger is displaced in a second direction, fluid is drawn into the fluid pump chamber.

16. The medical fluid pumping system of claim 11, wherein the base comprising a cylindrical projection that at least partially defines the fluid inlet port and the fluid outlet port, and the medical fluid cassette defines at least one fluid passageway that extends along a peripheral surface of the cylindrical projection.

17. The medical fluid pumping system of claim 13, wherein the seal further comprises a pin that connects the ball to a disk-shaped body of the seal.

18. The medical fluid pumping system of claim 14, further comprising a cover fixed to the ring.

19. The medical fluid pumping system of claim 18, wherein the cover is fixed relative to the base such that the rotatable member can rotate relative to the base, the ring, and the dust cover.

20. The medical fluid pumping system of claim 19, wherein the cover is attached to a membrane that is fixed to the base.

21. The medical fluid cassette of claim 15, wherein the base comprises a first end region and a second end region, the first end region being located farther from the membrane than the second end region, and the first end region defining a fluid inlet port and a fluid outlet port.

22. The medical fluid cassette of claim 15, wherein the base comprising a cylindrical projection that at least partially defines the fluid inlet port and the fluid outlet port, and the medical fluid cassette defines at least one fluid passageway that extends along a peripheral surface of the cylindrical projection.

23. The medical fluid cassette of claim 15, wherein the seal is disk-shaped.

24. The medical fluid cassette of claim 15, wherein the seal comprises a ball that matingly engages a socket defined in the rotatable member to allow the rotatable member to rotate relative to the seal.

25. The medical fluid cassette of claim 24, wherein the seal further comprises a pin that connects the ball to a disk-shaped body of the seal.

26. The medical fluid cassette of claim 15, wherein the rotatable member comprises a plug defining an annular channel and a ring disposed in the annular channel and configured to rotate relative to the plug.

27. The medical fluid cassette of claim 26, further comprising a cover fixed to the ring.

* * * * *

UNITED STATES PATENT AND TRADEMARK OFFICE
CERTIFICATE OF CORRECTION

PATENT NO.       : 9,011,114 B2
APPLICATION NO.  : 13/412182
DATED            : April 21, 2015
INVENTOR(S)      : Sean Farrell and Joseph Michael Fallon Page 1 of 1

It is certified that error appears in the above-identified patent and that said Letters Patent is hereby corrected as shown below:

Claims

In Claim 9, column 26, line 35, delete "the the" and insert --the--.

In Claim 9, column 26, line 35, delete "liquid tight" and insert --liquid-tight--.

Signed and Sealed this
Twenty-seventh Day of October, 2015

Michelle K. Lee
*Director of the United States Patent and Trademark Office*